United States Patent [19]

Hutcheson et al.

[11] Patent Number: 4,889,132

[45] Date of Patent: Dec. 26, 1989

[54] PORTABLE AUTOMATED BLOOD PRESSURE MONITORING APPARATUS AND METHOD

[75] Inventors: J. Stanford Hutcheson, Chapel Hill; Richard W. Lutz, Carrboro; Paul A. Obrist; David J. Flaugher, both of Chapel Hill; Charles E. Watts, Raleigh, all of N.C.

[73] Assignee: The University of North Carolina at Chapel Hill, Chapel Hill, N.C.

[21] Appl. No.: 913,677

[22] Filed: Sep. 26, 1986

[51] Int. Cl.$^4$ .................................................. A61B 5/04
[52] U.S. Cl. ..................................... 128/680; 128/683; 128/668
[58] Field of Search .............................. 128/680–683, 128/630, 663, 666–668

[56] References Cited

U.S. PATENT DOCUMENTS

| | | |
|---|---|---|
| 29,921 | 2/1879 | Cherry et al. . |
| 3,308,811 | 3/1967 | Gillette et al. . |
| 3,542,011 | 11/1970 | Langenbeck et al. . |
| 3,550,582 | 12/1970 | Wilhelmson . |
| 3,557,779 | 1/1971 | Weinstein . |
| 3,654,915 | 4/1972 | Sanctuary . |
| 3,704,708 | 12/1972 | Iberall . |
| 3,754,545 | 8/1973 | Weinstein . |
| 3,776,228 | 12/1973 | Semler . |
| 3,896,791 | 7/1975 | Ono . |
| 3,906,937 | 9/1975 | Aronson . |
| 3,906,939 | 9/1975 | Aronson . |
| 3,996,928 | 12/1976 | Marx . |
| 4,003,370 | 1/1977 | Emil et al. . |
| 4,073,011 | 2/1978 | Cherry et al. . |
| 4,097,113 | 6/1978 | McKelvy . |
| 4,106,495 | 8/1978 | Kennedy . |
| 4,108,166 | 8/1978 | Schmid . |
| 4,112,929 | 9/1978 | Affeldt et al. . |
| 4,120,294 | 10/1978 | Wolfe . |
| 4,123,785 | 10/1978 | Cherry et al. . |
| 4,211,238 | 7/1980 | Shu et al. . |
| 4,216,779 | 8/1980 | Squires et al. . |
| 4,219,398 | 5/1985 | Lisiecki et al. . |
| 4,228,506 | 10/1980 | Ripley et al. . |
| 4,248,241 | 2/1981 | Tacchi . |
| 4,248,242 | 2/1981 | Tamm . |
| 4,252,127 | 2/1981 | Gemelke . |
| 4,270,547 | 6/1981 | Steffen et al. . |
| 4,300,573 | 11/1981 | Rebbe et al. . |
| 4,313,445 | 2/1982 | Georgi . |
| 4,320,765 | 3/1982 | Cothignol et al. ................... 128/663 |
| 4,320,767 | 3/1982 | Villa-Real . |
| 4,339,800 | 7/1982 | Woods . |
| 4,378,807 | 4/1983 | Peterson et al. . |
| 4,383,534 | 5/1983 | Peters . |
| 4,397,317 | 8/1983 | Villa-Real . |
| 4,417,254 | 11/1983 | Woods . |
| 4,422,081 | 12/1983 | Woods . |
| 4,429,699 | 2/1984 | Hatschek . |
| 4,459,991 | 7/1984 | Hatschek . |
| 4,475,557 | 10/1984 | Hatschek et al. . |
| 4,483,346 | 11/1984 | Slavin . |
| 4,510,942 | 4/1985 | Miyamae et al. . |
| 4,513,753 | 4/1985 | Tabata et al. . |
| 4,592,365 | 6/1986 | Georgi ............................. 128/682 |

OTHER PUBLICATIONS

Article in Del Mar Avionics entitled "Pressurometer" Model 1978.

*Primary Examiner*—Francis Jaworski
*Attorney, Agent, or Firm*—Cushman, Darby & Cushman

[57] ABSTRACT

A portable auscultatory blood pressure and heart rate measurement system is wearable by an ambulatory patient and measures systolic and diastolic pressure upon request or at random time intervals within a user-programmed range. Cuff inflation pressure and deflation rate are also user programmable. During cuff deflation, pressure and korotkoff sound signal amplitudes are obtained and stored in timed relation to the user's ECG, a threshold level is derived from pressure signal amplitudes and system noise level, and systolic and diastolic pressure determined and validated by trend analysis in relation to this threshold level. Analysis results are stored along with a sample number and time of measurement under on-board digital signal processor control, in both a solid state memory and an analog serial data storage medium such as magnetic tape. Data may be retrieved by local display, for example, in a biofeedback setting, or display on an external video display or printer, or can be downloaded in digital form to a local or remote digital computer.

24 Claims, 21 Drawing Sheets

List continued on next page.

OTHER PUBLICATIONS

Paper entitled "Validation of the Vita-Stat Automated Noninvasive Blood Pressure Recording Device" by Dembroski and MacDougall from Eckerd College.

Committee Report entitled "Publication Guidelines for Heart Rate Studies in Man".

Article entitled "Advanced Medical Systems: An Assessment of the Contributions" by Edward J. Hinman, M.D., M.P.H., pp. 103-112.

Advertisement article by MEDTEK for a Blood Pressure Instrument Mini Monitor, BPI-520.

Advertisement Article by MEDTEK for Blood Pressure Monitor; BPI-420.

Patient Associated Literature; EKG & Blood Pressure Monitor, 9/13/76.

Article from the Encyclopedia of Computer Science and Engineering by Ralston and Reilly, Jr. for Random Access and Random Number Generation.

"Pressurometer III Ambulatory Blood Pressure Monitor Model 1978" by Del Mar Avionics of Irvine, California, 1979 product information bulletin.

"Validation of the Vita-Stat Automated Blood Pressure Recording Device" by Dembroski et al published in Herd et al, *Cardiovascular Instrumentation: Applicability of New Technology to Biobehavioral Research* (National Institute of Health, Bethesda, Maryland, 1983).

Two "BPI 520" advertisements published by Medtek of Carrollton, Texas (1979).

"A Microprocessor System to Measure Blood Pressure", *Advanced Medical Systems: An Assessment of the Contributions* (10th Annual Meeting of the Society for Advanced Medical Systems, Symposia Specialists), 1979, published by Smith, Hutcheson, Lutz & Hsiao of The University of No. Carolina at Chapel Hill, distributed by Year Book Medical Publishers, Chicago, Illinois.

"The Non-Invasive Measurement of Blood Pressure in Bio-Behavioral Research," Houston, Texas (May 16-19, 1982) by Obrist & Hutcheson, presented at the Working Conference on Cardiovascular Instrumentation: Applicability of New Technology to Bio-Behavioral Research.

Jennings et al, "Publication Guidelines for Heart Rate Studies in Man", 18, *Psychophysiology*, 226-231 (The Society for Psychophysiology Research, May, 1981).

Electronic Design, vol. 24, No. 19, Issued 13 Sep. '76, "Semis Invade Medical Transducers, uPs Monitor EKG and Blood Pressure".

(R-WAVE DIAGRAM)

(CUFF CYCLE)

CALIBRATE ROUTINE

RESET INTER-CYCLE TIMER ROUTINE

INFLATE (K SOUND DETECTION)

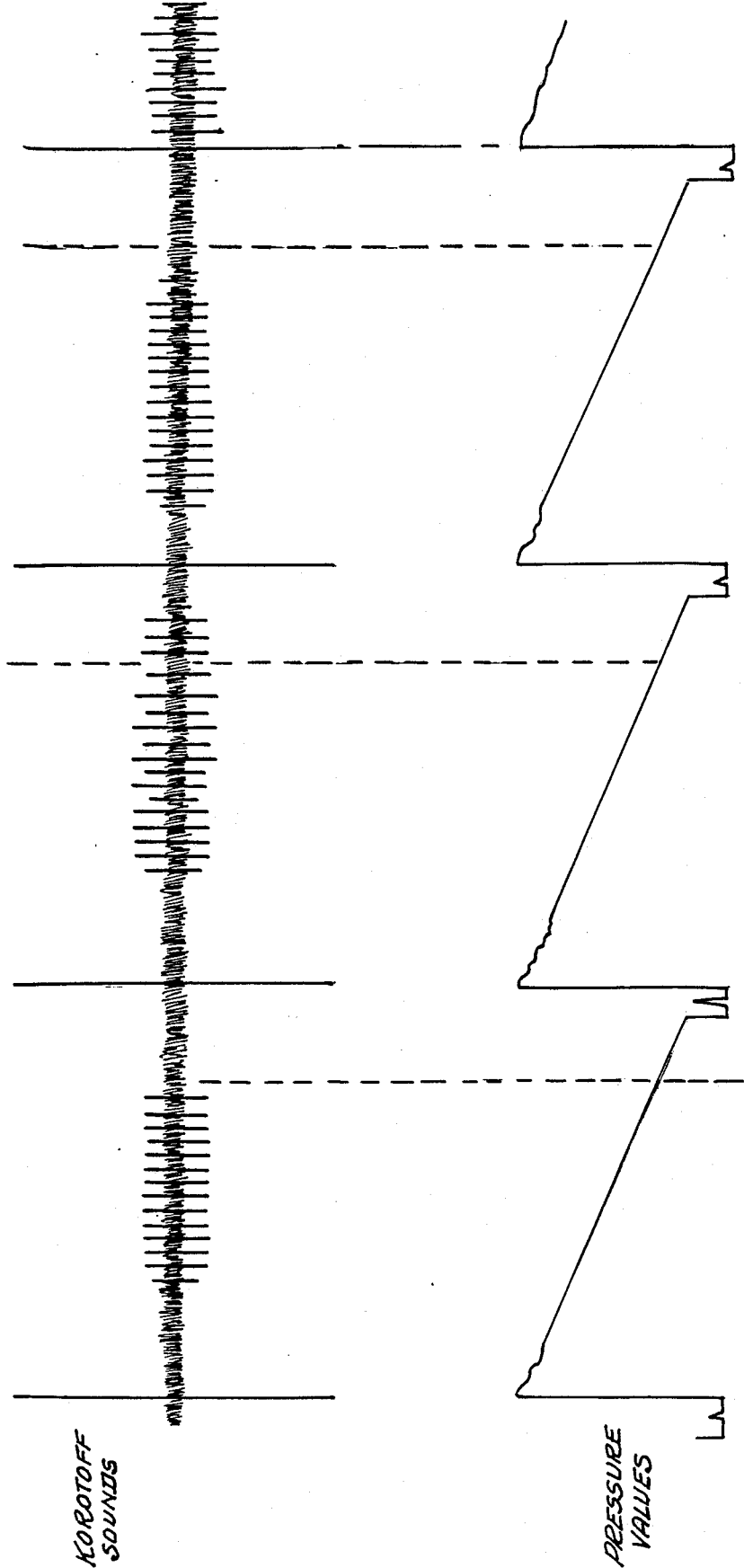

PORTABLE AUTOMATED BLOOD PRESSURE MONITORING APPARATUS AND METHOD

FIELD OF THE INVENTION

The present invention is related to medical devices which automatically evaluate the cardiovascular condition of a subject. More particularly, the present invention is related to systems and methods for measuring blood pressure and heart rate in mobile subjects over extended periods of time using non-invasive auscultatory techniques.

BACKGROUND OF THE INVENTION

Cardiovascular evaluation of a subject may be performed directly (such as by intra-arterial measurements) or indirectly (e.g., by the classic auscultatory method). Because of the dangers associated with the direct method of measurement, the auscultatory method has become nearly universally accepted as the method of choice by medical clinicians and researchers alike.

As is well known, the auscultatory method of determining the blood pressure of a patient makes use of the acoustical disturbances ("Korotkoff sounds" or "K-sounds") produced when blood flows through a compressed (occluded) artery. The physician typically positions an inflatable occluding cuff about the upper arm of the patient and positions the sensing orifice of a stethoscope between the cuff and the arm in the vicinity of the brachial artery. A squeeze-type air pump is used to inflate the occluding cuff to a pressure somewhat greater than the systolic blood pressure of the patient to completely occlude the brachial artery. No sounds are detected by the stethoscope when the artery is fully compressed by the cuff because of the absence of arterial blood flowing through the artery below the point of occlusion.

An air valve is operated by the physician to slowly deflate the cuff and thereby decrease the pressure it exerts upon the walls of the brachial artery while the cuff pressure is continuously monitored (e.g., by a mercury manometer or the like). When the pressure exerted by the cuff falls to slightly below the patient's systolic blood pressure, each cardiac systole produces a head front of blood forcing the walls of the brachial artery to exert a greater force against the occluding cuff than the cuff exerts in return, thereby causing the artery to become temporarily unoccluded. The temporary opening of the brachial artery under the force produced by the cardiac systole produces a Korotkoff sound which can be heard with the stethoscope. The physician notes the cuff pressure when he or she hears the first Korotkoff sound to obtain the systolic blood pressure of the patient.

The artery becomes occluded once again after the head front of blood produced by the cardiac systole passes through the point of occlusion, and remains occluded until the next cardiac systole occurs. A Korotkoff sound is produced for each contraction of the heart (delayed slightly from the time of systole by the time it takes the head front of blood to travel from the heart to the point of arterial occlusion) so long as the cuff pressure is greater than the diastolic blood pressure of the patient. The physician may count the number of Korotkoff sounds occurring during a given time interval to measure the heart rate of the patient.

The physician continues to slowly deflate the cuff until Korotkoff sounds are no longer heard in the stethoscope (indicating that the cuff no longer exerts sufficient pressure on the arterial wall to occlude the artery even during cardiac diastole). The physician notes the cuff pressure at this time as the diastolic blood pressure of the patient.

Non-invasive measurement of blood pressure and heart rate is useful for clinical, experimental and medical research purposes. For instance, such measuring techniques are useful for monitoring surgical patients in the operating or recovery room and for other clinical patient evaluation (such as clinical stress or exercise testing). Classic auscultatory measuring techniques performed by a trained individual can typically be used in clinical settings, but are impractical for other applications, such as the cardiovascular evaluation of mobile patients during their exposure to daily environmental stress or evaluation over extended periods of time. Portable devices capable of automatically obtaining cardiovascular data from an ambulatory subject have therefore been developed to make possible a wide range of cardiovascular research involving, for example, field studies, biofeedback studies, and patient behavioral modification.

A portable blood pressure monitoring system capable of obtaining cardiovascular information about a subject over long periods of time is described in U.S. Pat. No. 4,216,779 to Squires et al (issued Aug. 12, 1980) and a 1979 product information bulletin entitled "Pressurometer III Ambulatory Blood Pressure Monitor Model 1978" published by Del Mar Avionics of Irvine, Calif. The disclosed system non-invasively measures blood pressure and heart rate under electronic control using the auscultation method. An occlusion cuff is automatically inflated at predetermined programmable intervals to a level greater than and dependent upon the last-measured systolic pressure of the subject. The cuff is subsequently deflated at fixed decrements in response to R-waves detected by ECG electrodes, while a microphone senses Korotkoff sounds. The presence or absence of a Korotkoff sound within a preset interval following each heartbeat is used to determine when the cuff pressure (measured by an electronic pressure sensor) equals the systolic and diastolic blood pressures of the subject. Systolic and diastolic blood pressures corresponding to the first and last Korotkoff sounds detected during each cuff inflation-deflation cycle are converted into digital signals and displayed on an electronic display. The systolic and diastolic pressures are also recorded in digital form on a continuously-running portable tape recorder together with signals from the ECG electrodes. After a number of cycles of operation, the magnetic tape is removed from the recorder and inserted into an analyzer for high-speed play-back to obtain a plot of heart rate and accompanying blood pressure readings on a common chart.

U.S. Pat. No. 4,252,127 to Gemelke (issued Feb. 24, 1981) discloses a portable blood pressure device also having an automatically-inflatable occluding cuff, a Korotkoff sound sensor, a cuff pressure sensor, and a tape recorder. The occluding cuff is periodically automatically inflated and subsequently slowly deflated. A tape recorder is turned on when the cuff pressure begins to fall. The output of the Korotkoff sound microphone is gated by a signal produced by pulsations in cuff pressure caused by heartbeats, filtered, buffered, and applied to one input of a summing amplifier. The other input of the summing amplifier is connected to the voltage-encoded output of the cuff pressure sensor. The resulting composite output is modulated by a voltage-to-frequency converter to produce a waveform with constant off-time occurring at a variable frequency. This waveform is recorded on the tape recorder. Respective pressure and K-sound signals are later recovered individually by passing the playback signal from the tape recorder through a comparator, rectifier, frequency-to-voltage converter and filtering network. High-pass filtering eliminates the pressure signal from the demodulated composite signal, leaving the K-sound signals. The pressure signal is likewise recovered by filtering the demodulated composite signal with a low-pass filter.

Graham, M., "μPs Monitor EKG and Blood Pressure", 24 *Electronic Design* No. 19, p. 28 (Sept. 13, 1976) discloses a portable electrocardiogram and blood pressure signal monitor which processes information only when deviations are detected. Graham apparently suggested and tried a technique of matching Korotkoff sound frequency characteristics of each K-sound occurring in real time with those of previously-stored Korotkoff sound models corresponding to systolic and diastolic pressure. The 1976 Graham article includes a block diagram of a microprocessor-controlled medical monitor and an extremely brief description of his Korotkoff sound detection technique. The tape recorder as shown in the block diagram is connected directly to the MPU, indicating that data was stored on tape in digital format only.

U.S. Pat. No. 4,270,547 to Steffen et al (1981) discloses a vital signs monitoring system which converts analog measurements of cardiovascular parameters into digital form for display.

Other references disclosing blood pressure measuring devices using a magnetic tape recorder to store cardiovascular measurements include U.S. Pat. No. 4,211,238 to Shu et al (issued July 8, 1980) and U.S. Pat. No. 4,378,807 to Peterson et al (issued Apr. 5, 1983). U.S. Pat. No. 4,228,506 to Ripley et al (issued Oct. 14, 1980) discloses an intelligent data logging printer-plotter for use with a source of time-correlated digital systolic and diastolic blood pressure data and heart rate data.

Another automated non-invasive blood pressure recording device is disclosed in "Validation of the Vita-Stat Automated Blood Pressure Recording Device" by Dembroski et al, reprinted in Herd et al, *Cardiovascular Instrumentation: Applicability of New Technology to Biobehavioral Research* (National Institute of Health, Bethesda, Md. 1983). The system described in this publication includes an ambulatory data logging module with a removable random access memory pack and a base unit for interfacing the memory pack with a microcomputer. The logging module is programmed and initialized for measurements by loading information from the microcomputer into the memory pack. Cardiovascular measurements are automatically taken at fixed predetermined intervals and recorded in digital form in the memory. After measurements are completed, the memory pack is removed from the logging module and data stored in the memory pack is down-loaded via a data bus to a microcomputer for storing on a floppy disk, printing, analyzing, etc.

The following references disclose other cardiovascular data acquisition devices of possible relevance to the present application:
U.S. Pat. No. 3,654,915 to Sanctuary (1972);
U.S. Pat. No. 4,003,370 to Emil et al (1977);
U.S. Pat. No. 4,397,317 to Villa-Real (1983);
U.S. Pat. No. 4,383,534 to Peters (1983);
U.S. Pat. No. 4,248,241 to Tacchi (1981);
U.S. Pat. No. 4,519,398 to Lisiecki, et al.(1985);
U.S. Pat. No. 4,510,942 to Miyamae, et al (1985);
U.S. Pat. No. 4,475,557 to Hatschek, et al (1984);
U.S. Pat. No. 4,459,991 to Hatschek (1984);
U.S. Pat. No. 4,320,767 to Villa-Real (1982);
U.S. Pat. No. 4,248,242 to Tamm (1981);
U.S. Pat. No. 4,112,929 to Affeldt, et al (1978);
U.S. Pat. No. 3,996,928 to Marx (1976);
U.S. Pat. No. 3,776,228 to Semler (1973);
U.S. Pat. No. 3,550,582 to Wilhelmson (1970); and Two "BPI 520" advertisements published by Medtek of Carrollton, Tex. in June, 1983;

A paper published by Smith, Hutcheson, Lutz and Hsiao of The University of North Carolina at Chapel Hill entitled "A Microprocessor System To Measure Blood Pressure", *Advanced Medical Systems: An Assessment of the Contributions*, (10th Annual Meeting of the Society for Advanced Medical Systems, Symposia Specialists, 1979, distributed by Year Book Medical Publishers, Chicago, Ill.) describes a microprocessor-based system which automatically controls occluding cuff pressure and detects Korotkoff sounds only during a short window referenced to the EKG. A microcomputer is used to store and analyze data. See also Obrist & Hutcheson, "The Non-Invasive Measurement of Blood Pressure in Bio-Behavioral Research," presented at the "Working Conference on Cardiovascular Instrumentation: Applicability of New Technology to Biobehavioral Research," Houston, Tex. (May 16–19, 1982) (addressing methods for accurately identifying Korotkoff sounds); Obrist & Hutcheson, "An Automated Non-Invasive Blood Pressure Monitor: Principle of Operation and Reliability" (1979); and Jennings et al, "Publication Guidelines for Heart Rate Studies in Man," 18 *Psychophysiology* 226–31, (The Society for Psychophysiology Research, May, 1981).

The following references (believed to be less relevant than those cited above) disclose physiological parameter monitoring systems and/or components for use in such systems:

| U.S. Pat. No. | Inventor | Date |
| --- | --- | --- |
| 4,106,495 | Kennedy | 1978 |
| 4,339,800 | Woods | 1982 |
| 4,417,254 | Woods | 1983 |
| 4,422,081 | Woods | 1983 |
| 4,123,785 | Cherry, et al. | 1978 |
| Re. 29,921 | Cherry, et al. | 1979 |
| 4,073,011 | Cherry, et al. | 1978 |
| 4,513,753 | Tabata, et al. | 1985 |
| 4,483,346 | Slavin | 1984 |
| 4,429,699 | Hatschek | 1984 |
| 4,300,573 | Rebbe, et al. | 1981 |
| 4,120,294 | Wolfe | 1978 |
| 4,108,166 | Schmid | 1978 |
| 4,097,113 | McKelvy | 1978 |
| 3,906,939 | Aronson | 1975 |
| 3,906,937 | Aronson | 1975 |
| 3,896,791 | Ono | 1975 |
| 3,754,545 | Weinstein | 1973 |
| 3,704,708 | Iberall | 1972 |
| 3,557,779 | Weinstein | 1971 |
| 3,542,011 | Langenbeck | 1970 |

Many of the portable blood pressure monitoring systems disclosed in the cited references measure the systolic and diastolic blood pressure and heart rate of a subject automatically over an extended period of time. However, further improvements in such devices are necessary in order to increase reliability and accuracy. For example, presently-available ambulatory blood pressure monitoring systems use analysis algorithms which make decisions in real time based upon each Korotkoff sound as it occurs. The present applicants have discovered that this approach can (and frequently does) lead to erroneous pressure determinations because the measuring system has no way of determining if the signals appearing on the Korotkoff sound channel represent actual Korotkoff sounds associated with the Korotkoff sound envelope occurring between systolic and diastolic cuff pressure points, or whether the signals instead are caused by spurious noise and/or artifacts having frequency characteristics similar to Korotkoff sounds. Real-time signal processing techniques such as noise reduction and dynamic thresholding can partially but not completely eliminate errors introduced by these effects. Moreover, if a patient's Korotkoff sound profile suddenly changes drastically from one measurement cycle to the next, or worse yet, within a period during which the occluding cuff is being deflated, a system using real-time analysis of Korotkoff sounds cannot compensate for the changes in the Korotkoff sound envelope profile, and may determine blood pressure erroneously. Patents may be diagnosed incorrectly due to such errors, since there is no way to tell whether atypical measurements are caused by intermittent cardiovascular problems of the patient or by measurement errors.

SUMMARY OF THE INVENTION

The present invention automatically obtains cardiovascular information about a subject. In accordance with one feature of the present invention, an arbitrary time duration is selected and timed. At the conclusion of the timing of the arbitrary duration, at least one cardiovascular parameter of a subject is measured. A second arbitrary time duration is selected and timed, and the cardiovascular parameter is again measured. This process is repeated to obtain a plurality of measurements of the parameter.

The arbitrary time duration is preferably selected by producing a random number. The random number is tested to determine whether it falls within a predetermined range, and another random number is produced if the earlier obtained random value does not fall within the predetermined range. The time duration is set to a value proportional to the tested random number. The predetermined range may be programmable.

In accordance with another feature of the present invention, the measured cardiovascular parameter may comprise at least one of blood pressure and heart rate. An occluding cuff disposed on the subject is inflated to a pressure in excess of the systolic blood pressure of the subject. The pressure of the cuff is continuously sensed and controllably deflated. Korotkoff sounds produced by the subject during cuff deflation are sensed. Indicia of the sensed sounds and pressure are stored in analog form in a serial storage device. Indicia of blood pressure of the subject is produced in response to the sensed Korotkoff sounds and cuff pressure, and stored in a solid state memory device.

Indicia of blood pressure and heart rate are preferably produced by encoding systolic and diastolic blood pressure values in digital form, and producing a digital value corresponding to the heart rate of the subject. The encoded blood pressure values and heart rate are preferably stored in a random access semiconductor memory device. The stored digital indicia may be selectively transmitted to a peripheral device.

In accordance with another feature of the present invention, the pressure of the occluding cuff is maintained at the predetermined pressure in excess of the systolic blood pressure of the subject for a predetermined period of time.

In accordance with yet another feature of the present invention, data is stored during a cuff cycle and is analyzed at the end of the cuff cycle. The cuff is inflated to a pressure greater than the systolic blood pressure of the subject, and is then linearly deflated at a controlled rate until the pressure within the cuff falls to less than the diastolic blood pressure of the subject. During cuff deflation, a first signal is continuously produced indicating the amplitude of sounds detected by a Korotkoff sound transducer disposed on the subject. Also during cuff deflation, a second signal is produced which indicates the pressure within the cuff. The onset of each cardiac cycle of the subject is detected in response to signals generated by ECG electrodes coupled to the subject. For each detected cardiac cycle, the peak level PKS of the first signal is determined, the level PRE of the second signal occurring at the time of the peak level PKS is also determined, and the peak level PKS and the level PRE are stored in a storage device.

After cuff deflation, a predetermined number of consecutive cardiac cycles having the highest average peak level of the first signal PKS are determined in response to the peak levels PKS stored in the memory device. The mean level AKSN of all of the peak levels PKS stored in the storage device is calculated, and the mean value ANOISE of all of the peak levels PKS stored in the storage device which are less than the mean value AKSN is also calculated. A threshold value K-THRESHOLD is calculated as $$\frac{AKSN - ANOISE}{2} + ANOISE.$$

The stored peak level PKS measured for the last cardiac cycle occurring before the center one of the predetermined number of consecutive cardiac cycles having the highest average peak level which is less than K-THRESHOLD is determined, and the level PRE stored in the storage device for this last cardiac cycle is selected as the systolic blood pressure of the subject. Similarly, the stored peak level PKS measured for the first cardiac cycle occurring after the center one of the predetermined number of consecutive cardiac cycles having the highest average peak level of the first signal which is less than K-THRESHOLD is determined, and the level PRE stored in the storage device for this first cardiac cycle is selected as the diastolic blood pressure of the subject.

The portable computer-based blood pressure monitoring system in accordance with the present invention provides a wearable instrument including analog and digital signal processing modules, an air pump, at least one electronic air valve, a battery pack and a micro-cassette tape recorder. The entire system is housed in a relative small molded plastic case weighing less than five pounds and carried in a leather pouch suspended from the patient by means of a shoulder strap and belt around the patient's waist.

The system measures systolic and diastolic blood pressure and heart rate of mobile subjects over extended periods of time and records the measurements together with the coordinate in real time at which they were obtained. The system automatically performs classic non-invasive auscultatory techniques using a standard blood pressure cuff, a piezoelectric Korotkoff microphone, a microswitch cuff pressure transducer and ECG electrodes. The entire system is automatically controlled by an on-board digital signal processor. The system measures systolic and diastolic pressure and heart rate and analyzes this cardiovascular data. The results of the analysis are stored together with sample number and the real time (e.g. in hours ad minutes) at which the measurements were obtained in digital form in a semiconductor memory. Measurements are spaced at either fixed or random intervals (at user selection) for periods of time up to and exceeding 24 hours. The system also stores the results of measurements on an analog serial data storage medium (such as magnetic tape) in the form of analog signals.

The recorded data may be retrieved in several ways. At the end of each measurement ("cuff") cycle, the systolic and diastolic blood pressure and heart rate values are suitably displayed on an electronic display device to facilitate biofeedback treatment applications. The same data may also be displayed on an external video display device or printed by a hard-copy printer at the end of each cuff cycle. Following a complete recording period including many cuff cycles, the recorded data can be down-loaded in digital form via a serial data link to an external digital computer for additional processing or storage, or it can be displayed on a data terminal, printer, etc. The data may also be transmitted over conventional land lines to a remote location using a modem.

All important operating parameters for the blood pressure monitoring system (including maximum cuff pressure, rate of cuff deflation, and fixed or random inter-sample interval timing) are programmable by the user. The user can selectively operate the system in a manual mode (wherein measurement are made only upon request) or in an automatic mode (wherein a cuff measurement cycle occurs at the end of each selected time interval). The inter-sample time can be set to either a fixed (programmable) interval, or randomly selected from a programmable range of intervals.

In addition to acquiring and storing blood pressure and heart rate data in digital form, the system in accordance with the present invention uses an analog tape recording device for independently storing measurement information in analog form. The analog information stored on the tape can be used to validate on-board digital signal processing accuracy, and permits the user to recover the original cuff pressure signal and corresponding Korotkoff sounds on a strip-chart recorder or the like for manual and visual analysis.

BRIEF DESCRIPTION OF THE DRAWINGS

These and other features of this invention will be more completely appreciated by reading the following detailed description taken in conjunction with the accompanying drawings, of which:

FIG. 13 is a graphical illustration of exemplary output signals obtained from the decoder shown in FIG. 12;

BRIEF DESCRIPTION OF THE PREFERRED EMBODIMENT

Figure 1:
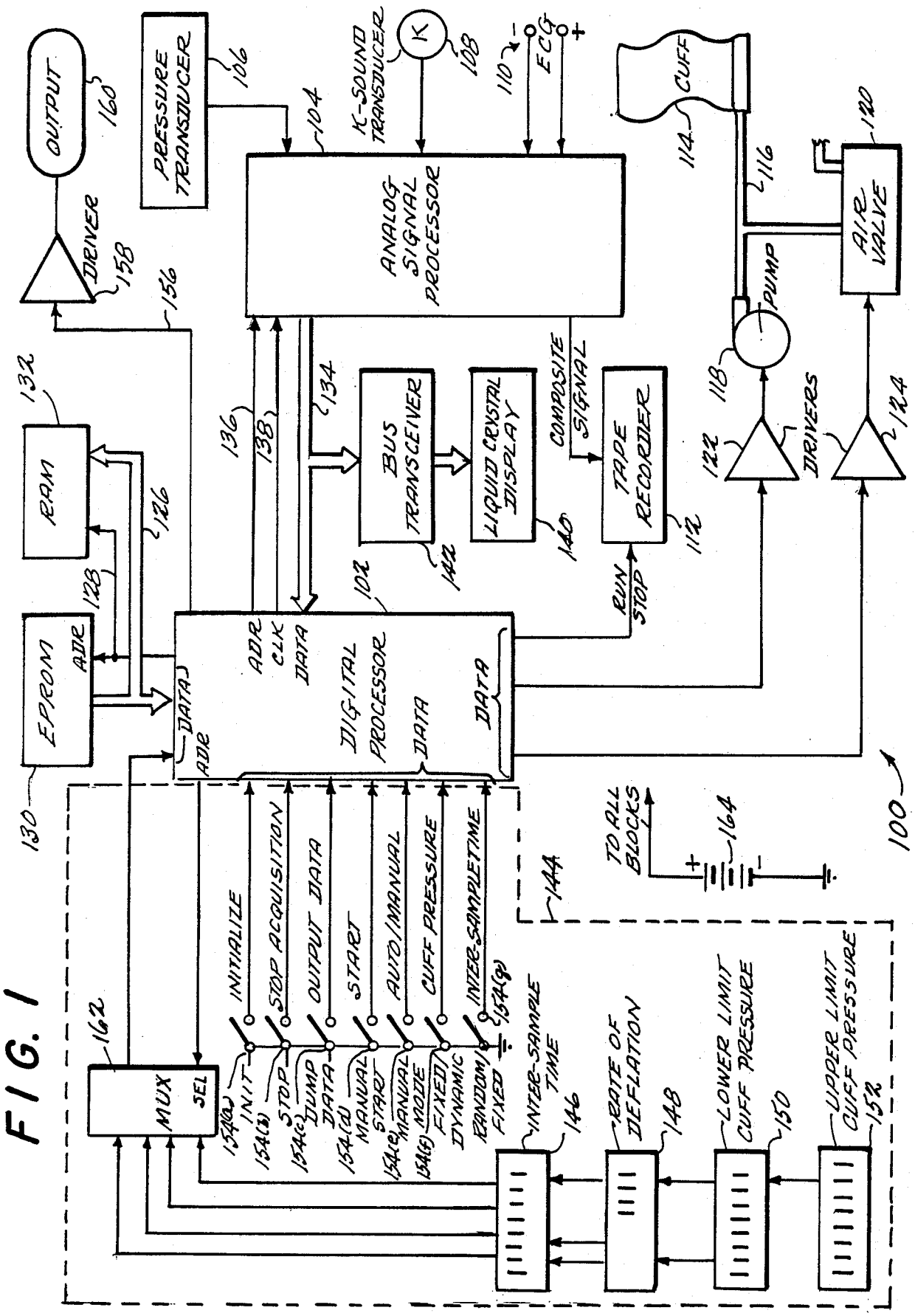
FIG. 1 is a block schematic diagram of the presently preferred exemplary embodiment of a system 100 in accordance with the present invention.

FIG. 1 is a block diagram of the presently preferred exemplary embodiment of a system 100 in accordance with the present invention. System 100 includes a digital signal processor 102 and an analog signal processor 104. Three sensors input signals to analog signal processor 104: a pressure transducer 106, a Korotkoff sound (K-sound) transducer 108, and ECG electrodes 110. Analog signal processor 104 samples the analog outputs of pressure transducer 106, K-sound transducer 108 and ECG electrodes 110, converts the sampled signals to digital signal levels, and transmits the digital signals to digital processor 102. Analog signal processor 104 also combines the sampled signals from pressure transducer 106 and K-sound transducer 108 into a composite analog signal and applies the composite signal to the signal input of a conventional audio tape recorder 112. Digital processor 102 controls the transport of recorder 112.

A conventional occluding arm pressure cuff ("cuff") 114 is connected by tubing 116 to an air pump 118 and to an air valve 120. Air valve 120 in the preferred embodiment comprises an electronic "minimatic" valve manufactured by Clippard Instrument Laboratory of Cincinnatti, Ohio. Air pump 118 may comprise any conventional, compact, lightweight, low-power air compressor capable of producing at least 250 mmHg of pressure (any source of pressurized fluid, such as a pressurized tank of gas or liquid, could be substituted for pump 118). Pump 118 and valve 120 are preferably encapsulated in acoustical foam for noise reduction. An additional electrically actuatable valve (not shown) may be provided at the output of pump 118 to prevent air from leaking out of cuff 114 through the pump when the pump is off.

Pressure transducer 106 is connected to cuff 114 via an additional section of tubing (not shown) to somewhat isolate the transducer from the pressure variations produced when pump 118 is on. Pressure transducer 106 in the preferred embodiment comprises a Model 130PC Gage pressure transducer manufactured by Microswitch, Inc. Pressure transducer 106 produces an electrical signal the amplitude of which is directly proportional to the pressure within cuff 114 above ambient room (atmospheric) pressure, thereby enabling digital processor 102 to monitor the instantaneous pressure within the cuff. Digital processor 102 selectively actuates pump 118 (via a driver 122) to apply pressurized air through tubing 116 to cuff 114, thereby inflating the cuff. Digital processor 102 also selectively (and preferably alternatively) opens air valve 120 (via a driver 124) to release pressure from cuff 114. By selectively alternately actuating pump 118 and air valve 120 in response to the signals produced by pressure transducer 106, digital processor 102 controls the instantaneous pressure within cuff 114 to an extremely high degree of accuracy ($\pm 1$ mmHg).

In the preferred embodiment, digital signal processor 102 comprises a model MMC/02A Microsport CMOS microcomputer manufactured by R. J. Brachman Associates of Havertown, Pa. Digital processor 102 includes a low power 6502 CMOS microprocessor, four 6522 8-bit I/O port controllers (one 6521 CMOS controller may be substituted instead), a plurality of 16-bit software-controllable timers, interrupt facilities, etc. Digital processor 102 is connected via a bidirectional data bus 126 and an address bus 128 to an electrically-programmable read only memory (EPROM) 130 (such as a 27C16 EPROM chip) and to a random access memory (RAM) 132 (which provides a stack storage facility for the digital processor). Program instructions ("firmware") are stored in EPROM 130 in a conventional fashion, while RAM 132 stores digital information obtained during the operation of system 100.

Digital processor 102 is connected via a second bidirectional data bus 134 and a second address bus 136 to analog signal processor 104 (if desired, data buses 126 and 134 could comprise the same data bus, and address buses 128 and 136 could comprise the same address bus). Digital processor 102 also provides a clock signal to analog signal processor 104 via a clock line 138 to synchronize the analog signal processor with digital processor 102. Digital processor 102 is also connected via data bus 134 and a conventional bus transceiver 142 to a conventional liquid crystal display (LCD) 140 (LCD 140 in the preferred embodiment comprises a Model PCIM 200 Display Unit manufactured by Printed Circuits International of Sunnyvale, Calif.). Digital processor 102 may selectively display alphanumeric information on liquid crystal display 140 by writing appropriate information to it via data bus 134 and a bus transceiver 142.

A user may selectively program information to system 100 via a user interface device 144. Interface device may comprise any conventional means for permitting a user to input information to digital processor 102 (e.g. arrays of discrete switches, "DIP" (dual in-line package) switches, a conventional keyboard or keypad, etc.) In the preferred embodiment, interface device 144 includes respective arrays of "DIP" switches 146, 148, 150 and 152 and an array of discrete single pole single throw (SPST) switches 154(a)–154(g). Each of switches 154(a)–154(g) is preferably dedicated to a different command to be directed to system 100.

In the preferred embodiment, "INIT" switch 154(a) is depressed to initialize system 100, "START" switch 154(d) is depressed to cause the system to begin acquiring data, and "STOP" switch 154(b) is depressed to stop data acquisition. The depression of "DUMP DATA" switch 154(c) causes digital processor 102 to transmit data stored in RAM 132 in serial form down a serial data output line 156 via driver 158 to an output connector 160. "AUTO/MANUAL" Switch 154(e) selects whether system 100 automatically initiates cuff cycles or whether cuff cycles are to be initiated only upon depression of "START" button 154(d). "FIXED/DYNAMIC" switch 154(f) determines whether cuff 114 is to be inflated to a predetermined fixed cuff pressure determined by the setting of "Upper Limit Cuff Pressure" thumbswitch array 152, or whether the cuff inflation pressure is to be determined from previously-measured systolic blood pressure of the patient. "RANDOM/FIXED" switch 154(g) selects between a fixed inter-sample time (wherein cuff cycles occur at regular intervals the length of which are determined by "Inter-Sample Time" "DIP" switches 146) or at random time intervals (wherein the setting of "Inter-Sample Time" "DIP" switches 146 merely specifies a range from which a random inter-sample time interval is selected by system 100). The positions of "Lower Limit Cuff Pressure" "DIP" switches 150 specify the minimum cuff pressure at which measurements are to be taken. "Rate of Deflation" "DIP" switches 148 determine the rate of deflation of cuff 114, as will be explained shortly.

Lines connect switches 154(a)–154(g) directly to a data port of digital processor 102, while "DIP" switches 146, 152 are connected to digital processor 102 via a conventional data multiplexer 162. Digital processor 102 periodically ascertains the position of each of switches 154(a)–154(g) (after debouncing performed in a conventional manner) to determine if the user has inputted any new commands to system 100. Digital processor 102 selectively reads the settings of "DIP" switches 146–152 as required. The significance of the commands and data programmable via switches 154(a)–154(g) and "DIP" switches 146–152 will be more fully explained in connection with FIGS. 5–9.

Switches 154(a)–154(d) are preferably spring-loaded normally OFF switches (such as push buttons or the like) while switches 154(e)–154(g) are preferably toggle switches. Some of SPST switches 154(e)–154(g) could be eliminated and their function performed, for example, by a most-significant place switch of a corresponding one of "DIP" switches 146–152. Of course, it will be understood that any conventional data entry device could be substituted for the SPST switches and "DIP" switches shown. For instance, a compact numeric or alphanumeric keypad could be used in conjunction with LCD display 140 and a software (user-prompting type) data entry routine to facilitate data entry. Moreover, user interface device 144 need not be permanently connected to digital processor 102, but could comprise a separate control module to be connected only at the physician's office (to prevent the patient from manipulating the controls of the system during the testing procedure). For instance, control information could originate at a portable computer and be down-loaded to system 100 in a conventional manner.

System 100 is powered by batteries 164, which preferably are relatively light-weight, rechargeable and have sufficient capacity to power system 100 for at least 25 hours (in the preferred embodiment, batteries 164 comprise two 6-volt cells with a total capacity of 4.8 amp-hours). Batteries 164 could, of course, be used in conjunction with an auxiliary power source such as solar cells, an external battery recharger or the like. Tape recorder 112 is preferably powered by batteries 164 via a voltage regulator (not shown) to ensure that intermittent operation of pump 118 and air valve 120 does not substantially alter the tape speed of the tape recorder and, perhaps more importantly, to provide a TTL signal level controllable switching means by which digital processor 102 may switch the tape recorder on and off.

Figure 2:
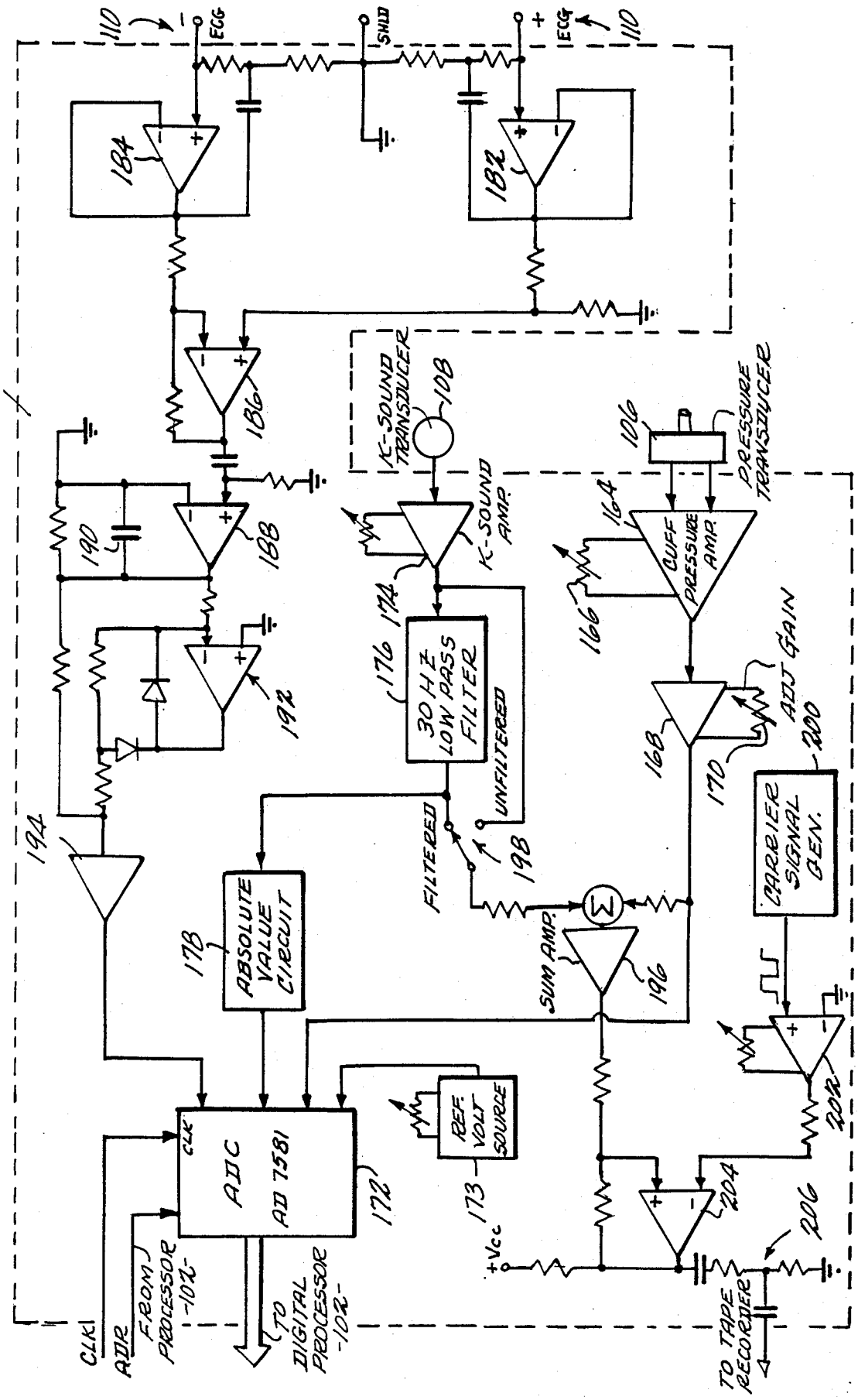
FIG. 2 is a schematic diagram of the analog signal processor shown in FIG. 1.

FIG. 2 shows a schematic diagram of analog signal processor 104. Analog signal processor 104 amplifies and conditions the signals produced by pressure transducer 106, K-sound transducer 108 and ECG electrodes 110, converts these signal levels to digital values, and selectively passes the digital values along to digital processor 102 in response to a request from the digital processor. Analog processor 104 also sums the analog signals produced by pressure transducer 106 and K-sound transducer 108, modulates a carrier signal with the summed signal, and applies the modulated envelope to the audio input of tape recorder 112 to be stored by the tape recorder in analog form for later recovery.

In the preferred embodiment, pressure transducer 106 is connected to a conventional bridge circuit (not shown) and produces a full scale output voltage of 30 millivolts at 250 mmHg cuff pressure with four volts of excitation. Amplifier 164 in the preferred embodiment comprises an AD524 precision instrumentation amplifier manufactured by Analog Devices, which provides high linearity, high common mode rejection, low offset voltage drift and low noise. In the preferred embodiment, amplifier 164 has a gain of approximately 100. A potentiometer 166 connected to the input null terminals of cuff pressure amplifier 164 can be adjusted to provide zero offset voltage, thereby causing a zero signal level output of the amplifier to exactly correspond to detection of atmospheric pressure (i.e. zero cuff pressure) by pressure transducer 106. The output of cuff pressure amplifier 164 is connected to the input of an additional active amplifier 168 (the gain of which may be adjusted with a potentiometer 170, but which is centered around approximately 133) to allow the full-scale pressure signal output of pressure transducer 106 (corresponding to a cuff pressure of 250 mmHg) to be converted to a full-scale input voltage requirement (4.00 volts) of analog-to-digital converter (ADC) 172.

K-sound transducer 108 in the preferred embodiment comprises a conventional piezoelectric Korotkoff sounds microphone (part No. 705-0018) manufactured by Narco Bio-Systems, Inc. of Houston, Tex. K-sound transducer 108 is preferably placed over the brachial artery of the patient under the bicep with cuff 114 retaining it in place. The output of K-sound transducer 108 is connected to the input of an active, adjustable-gain amplifier 174 which amplifies the output of the transducer to a convenient level for inputting to ADC 172. The output of amplifier 174 is connected to the input of a conventional active 30 hertz low pass filter 176 which has a roll-off rate in the preferred embodiment of 12 dB per octave.

Low pass filter 176 removes all of the signals from the output of amplifier 174 except those derived from Korotkoff sounds (which have a maximum amplitude of 18–22 Hz at systolic cuff pressure levels and 40–50 Hz at diastolic pressure levels). Amplifier 174 and filter 176 together produce a signal corresponding to the dominant frequency components (and the amplitudes thereof) of K-sounds detected by K-sound transducer 108 with high signal-to-noise ratio (S/N) while removing artifacts and other extraneous noise present at the input of amplifier 174 (such as noise caused by movement of the arm of the patient, flexing of the arm muscles, deflation of cuff 114, 60 Hz power line pick-up, etc). The output of filter 176 is applied to the input of an absolute value circuit 178 conventional in design which produces a signal equal to the absolute magnitude of the Korotkoff sounds measured by pressure transducer 108 regardless of the polarity of the K-sounds detected. The output of absolute value circuit 178 is connected to an input channel of ADC 172.

ECG electrodes 110 comprise a conventional ECG electrode array which are positioned in electrical contact with the skin of the patient (the ECG electrodes may be positioned in standard medical placement, coated with conventional electrode paste, and taped to the surface of the skin). The one of ECG electrodes 110 having a positive (+) polarity is connected to the input of a first unity gain operational amplifier 182 and the one of ECG having a negative (−) polarity is connected to a second unity gain operational amplifier 184. The circuit comprising amplifiers 182 and 184 has extremely high AC input impedance (on the order of $10^{12}$ ohms) and very high gain (2500) to amplify detected ECG signals from the millivolt range to approximately 4 volts. Feedback is used to obtain relatively a low DC impedance for amplifier biasing stability and to reduce electrode signal loading.

The outputs of operational amplifiers 182 and 184 are connected to respective inputs of a summing amplifier 186. The output of summing amplifier 186 is connected to a second amplifier 188. A capacitor 190 is provided in the feedback loop of an amp 188 to bypass high-frequency noise which may be picked up by the leads connecting ECG electrodes 110 to amplifiers 182 and 184. The output of amplifier 188 is connected to the input of a conventional absolute value circuit 192 which prevents R-waves from being inverted if the ECG electrodes are applied to the patient with the leads reversed. The output of absolute value circuit 192 is connected to an input channel of ADC 172 via an additional buffer amplifier 194.

ADC 172 in the preferred embodiment is a microprocessor-compatible eight bit, eight channel, memory buffered AD7581KN monolithic data acquisition system manufactured by Analog Devices of Norwood, Mass. ADC 172 includes an eight bit successive approximation A/D converter, an eight channel analog multiplexer, a dual port RAM with eight words of data buffer storage area, address latches and microprocessor compatible control logic. The successive approximation conversion performed by ADC 172 takes place on a continuous, channel-sequencing basis (i.e. sequencing between signals produced by pressure transducer 106, K-sound transducer 108 and ECG electrodes 110) using control signals producing digital signal processor 102 for synchronization. Data is automatically transferred to a predetermined location in a RAM internal to ADC 172 at the end of each conversion. Digital processor 102 may then address ADC 172 to selectively read the acquired, converted signals produced by pressure transducer 106, K-sound transducers 108 and ECG electrodes 110. A reference voltage source 173 produces a signal of −4.00 volts in a conventional manner and applies this reference voltage to a reference voltage input ADC 172 to provide a CMOS-level analog-to-digital converter output.

The amplified output of pressure transducer 106 appearing at the output of amplifier 168 is also connected to one input of a summing amplifier 196. The other input of summing amplifier 196 is connected to the common pole of a single pole double throw (SPDT) switch 198. Switch 198 alternately connects one of the amplified Korotkoff sound signals produced at the output of amplifier 174 and the Korotkoff sound signals after they have been filtered by low pass filter 176 to the other input of summing amplifier 196. The Korotkoff sound signals as applied to the input of summing amplifier 196 are bidirectional (since they have not been processed by absolute value circuit 178). The user may select either the filtered or unfiltered K-sound signals to be passed onto summing amplifier 196, depending upon the sort of signal analysis to be performed.

Summing amplifier 196 produces a composite signal at its output consisting of Korotkoff sound signals superimposed on the cuff pressure signal. Hence, summing amplifier 196 produces a single electrical signal containing information about two parameters of interest. A conventional carrier signal generator 200 (an NE556 function generator IC in the preferred embodiment) produces a symmetrical linear triangle-wave signal having a constant frequency of 150 Hz. The output of carrier signal generator 200 is applied to the input of an adjustable-gain amplifier 202. The output of amplifier 202 is connected to one input of a summing amplifier 204, and the output of summing amplifier 196 is connected to the other input of summing amplifier 204. Summing amplifier 204 functions as a pulse-width modulator, producing a low-level biphasic pulse-width modulated fixed-period signal with a duty cycle which changes in a linear manner with both measured pressure and Korotkoff sounds. The gain of amplifier 202 is adjusted so that a full cuff pressure range value of 250 mmHg yields a duty cycle (modulation percentage) at the output of summing amplifier 204 of 80%.

The output of amplifier 204 is connected to the audio input of tape recorder 112 (which in the preferred embodiment comprises a model 100B microcassette tape recording unit manufactured by the Sony Corporation) where it is recorded on a conventional audio microcassette tape. A passive impedance matching circuit 206 interfaces the output of amplifier 204 with the audio input of tape recorder 112.

Figure 3:
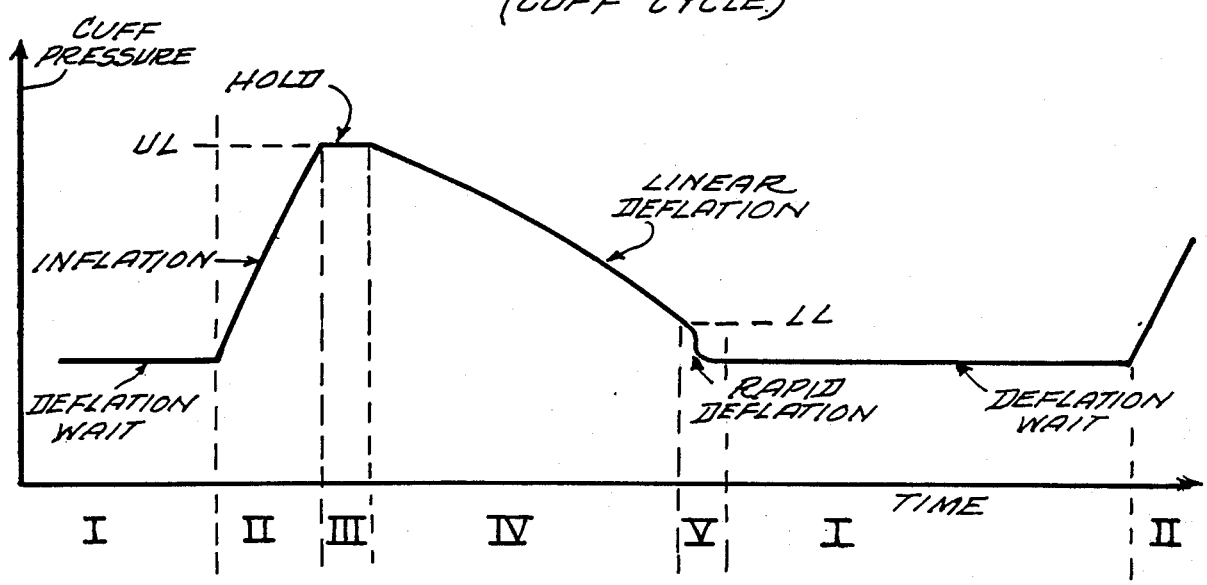
FIG. 3 is a graphical illustration of the pressure in the cuff 114 with respect to time during a cuff cycle in accordance with the present invention.
Figure 4:
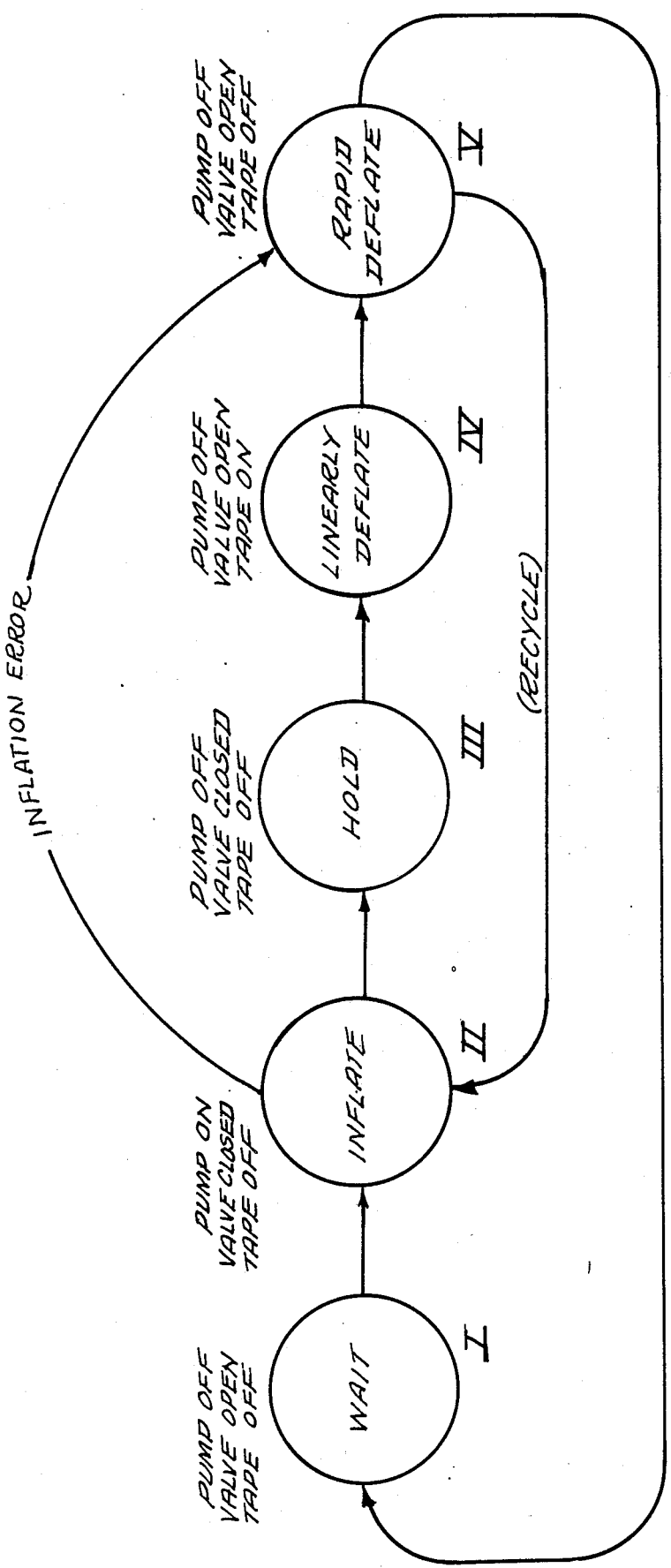
FIG. 4 is a state diagram corresponding to the cuff cycle in accordance with the present invention.

The operation of system 100 can be better understood by studying FIG. 3, which shows a graphical illustration of cuff pressure versus time for one cuff cycle, and FIG. 4, which shows a state diagram for the system. The preferred embodiment of system 100 has five states: "wait" (i), "inflate" (ii), "hold" (iii), "linearly deflate" (iv), and "rapid deflate" (v). Generally, states (i)-(v) are repeatedly performed in sequence by system 100 to obtain measurements of the patient's blood pressure and heart rate.

System 100 operates in the "wait" state (i) most of the time. In the "wait" state, cuff 114 is completely deflated (i.e. air valve 120 is open and pump 118 is off), and no information is being acquired the system (i.e. tape recorder 112 is off). System 100 remains in the "wait" state (i) until an event triggering a cuff cycle occurs. Events triggering the onset of a cuff cycle may include depression of "START" button 154(d) (if system 100 is operating in the manual mode), or the end of a preselected (either fixed or random) intersample time interval (when the system is operating in the automatic mode), as will be explained shortly. When an event triggering a cuff cycle occurs, system 100 enters the "inflate" state (ii).

In the "inflate" state (ii), cuff 114 is rapidly inflated (i.e. pump 118 is activated and air valve 120 is closed). During the "inflate" state (ii) in the preferred embodiment, no measurements are conducted, i.e. tape recorder 112 is off (of course, some measurements could be performed during cuff inflation instead of or in addition to during cuff deflation if desired). As will be explained, if the pressure of cuff 114 as sensed by pressure transducer 106 fails to reach a desired level within a predetermined period of time (e.g. 20 seconds), the cuff cycle is terminated (system 100 assumes that there is an air leak in cuff 114 or there exists some other reason why the cuff cannot be fully inflated), and the system proceeds directly to the "rapid deflate" state (v). However, if cuff 114 is successfully inflated to its desired "upper-limit" pressure (which may be user-programmed, as will be explained), system 100 proceeds directly into the "hold" state (iii).

In the "hold" state (iii), system 100 simply maintains the pressure of cuff 114 constant at its upper-limit pressure level (i.e. pump 118 is turned off and air valve 120 remains closed). Because pneumatic ringing present in cuff 114 immediately after "inflate" state (ii) could be mistaken by system 100 for K-sounds, no measurements are performed in the "hold" state (iii) i.e. tape recorder 112 remains off). System 100 remains in the "hold" state (iii) for a predetermined period of time (suitably one second) to permit pneumatic ringing in cuff 114 to be dampened. After the "hold" period has expired, system 100 proceeds to the "linear deflate" state (iv).

Measurements of blood pressure and heart rate are performed by system 100 during the "linearly deflate" state (iv). During the "linear deflate" state, air valve 120 is selectively opened under the control of digital processor 102 to cause the pressure in cuff 114 to slowly deflate at a linear rate. Digital processor 102 causes the pressure of cuff 114 to track a predetermined linear deflation profile (which may be stored in RAM 132 or EPROM 130 as a software model) by monitoring the signals produced by pressure transducer 106 and selectively opening and closing air valve 120 (pump 118 could, of course, be selectively activated if the cuff pressure falls too far below the profile level; however, it has been found that air valve 120 can be controlled precisely enough to ensure that actual cuff pressure closely tracks desired cuff pressure during deflation).

During the "linearly deflate" state IV, air value 120 is alternately opened and closed by processor 102, which varies the duration of periods during which the valve is opened to achieve desired instantaneous cuff pressures. As will be explained, parameters of the cuff pressure profile can be selected by the user.

During the "linear deflate" state (iv), system 100 acquires information of blood pressure and heart rate from K-sound transducer 108 and ECG electrodes 110, processes this information to obtain heart rate and blood pressure measurements, stores the measurements in RAM 132, and displays the measurements on LCD 140. In addition, tape recorder 112 is operated during the "linear deflate" state (iv) to record K-sound and cuff pressure information in analog form. When the cuff pressure falls below a predetermined (user-selectable) lower limit cuff pressure (preferably lower than the diastolic blood pressure of the subject), system 100 proceeds to the "rapid deflate" step (v).

During the "rapid deflate" step (v), any remaining pressure (above ambient atmospheric pressure) in cuff 114 is rapidly removed by opening air valve 120. Pump 118 remains off during this state, and no measurements are made. Cuff 114 is deflated as rapidly as possible to minimize patient discomfort. After cuff 114 is fully deflated, system 100 enters the "wait" state (i) once again to wait for the next cuff cycle to begin.

FIGS. 5-9 show main flow charts of the steps performed by system 100. The steps shown in these flow charts are performed by or under the control of digital signal processor 102 in accordance with firmware stored in EPROM 130 in the preferred embodiment. Of course, digital processor 102 could comprise any sort of device capable of carrying out a sequence of predetermined steps (e.g. a sequential state machine implemented with discrete logic components), and thus, the flow charts need not necessarily be performed under software control (although the facility to alter the steps performed by system 100 merely by changing the contents of EPROM 130 lends versatility to the system and therefore decreases its cost and increases its utility). In the flow charts, flow is generally from top to bottom.

Figure 5:
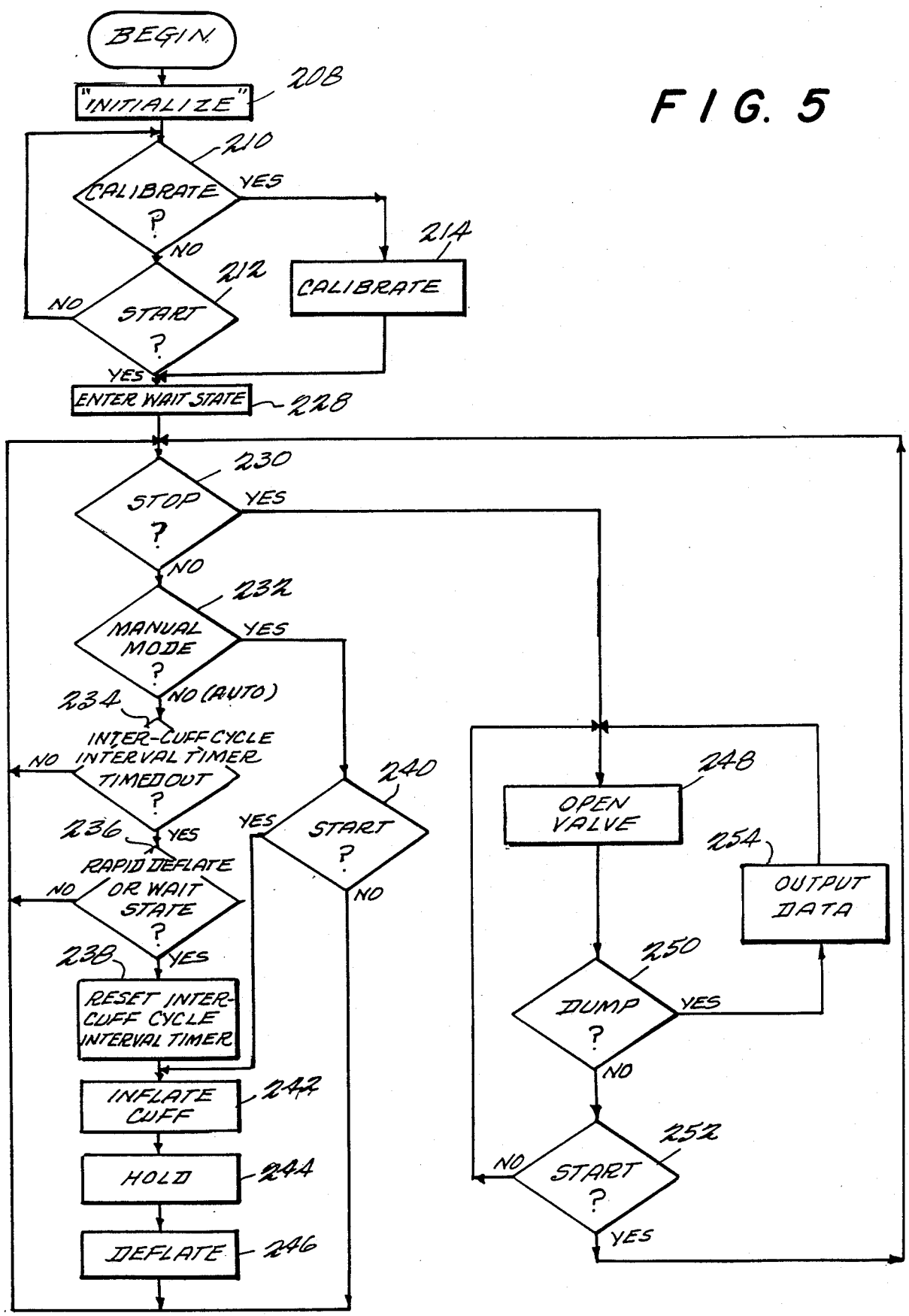
FIG. 5 is a main flow chart of the steps performed by the system shown in FIG. 1.

FIG. 5 is a main flow chart of the steps performed by digital processor 102. Initialization block 208 is performed only once, immediately after each power-on or reset. Initialization block 208 initializes and configures all programmable hardware in system 100 (e.g., analog signal processor 104, LCD 140, etc.) and initializes digital processor 102 itself (e.g., initializes processor registers, timers and stacks, I/O interface ports, software clocks, etc.). Initialization block 208 may cause processor 102 to display appropriate prompt indicia on LCD 140 to request a user to input the time of day and other information via user interface device 144. The inputted real time information is used to initialize a real time clock (which may comprise a storage location in RAM 132 or a programmable timer in digital processor 102). Initialization block 208 may also perform a self-testing diagnostic routine to ensure that all components of system 100 are operating properly, and may display indicia of any malfunctions which are detected.

After initialization has been performed (block 208), a continuous loop comprising decision blocks 210 and 212 are performed to await a command to be input by the user. The user may either begin normal data acquisition (by depressing the "START" button 154(d)), or request calibration (in the preferred embodiment, by depressing the "START" button 154(d) and the "DATA DUMP" button 154(c) simultaneously). If the user requests a calibration (decision block 210), calibrate block 214 is performed. Otherwise, system 100 awaits the depression of the "START" button 154(d) (decision block 212) before proceeding further.

Figure 6:
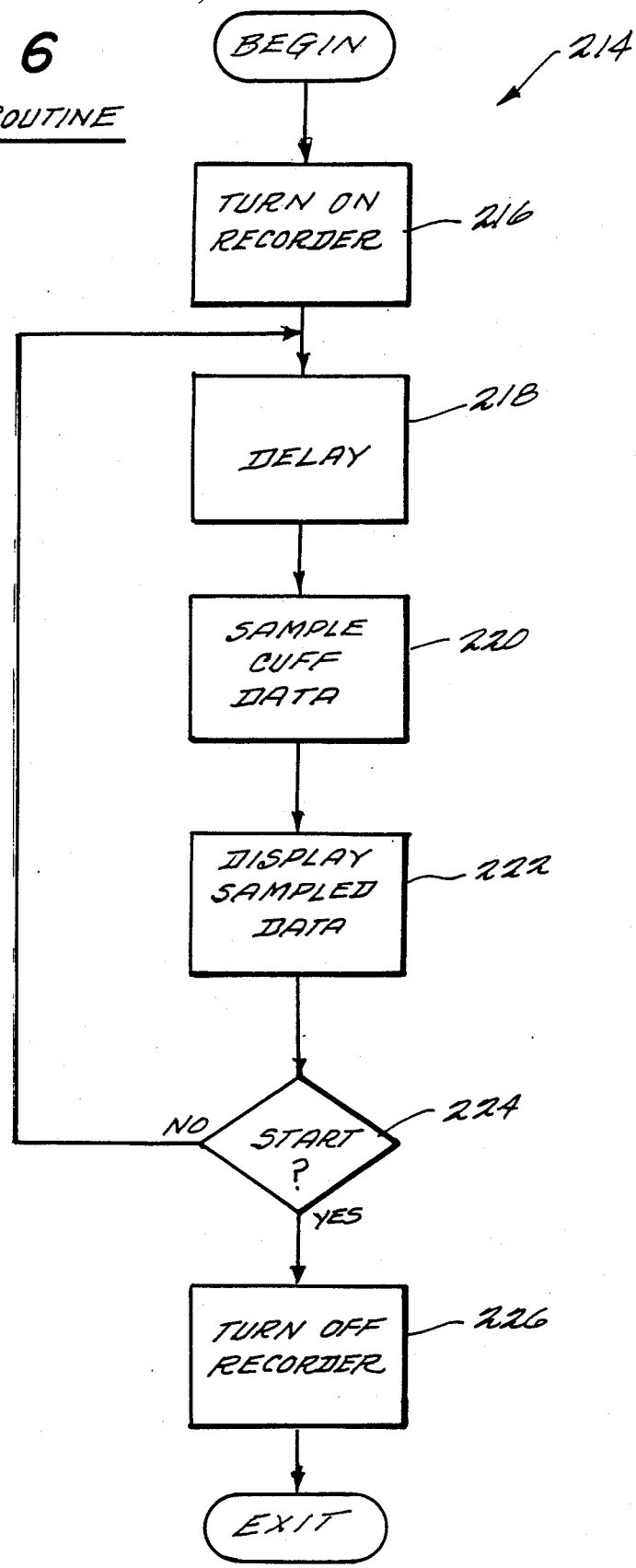
FIG. 6 is a detailed flow chart of the calibrate block shown in FIG. 5.

FIG. 6 is a detailed flow chart of a calibrate routine represented by the "calibrate" block 214 shown in FIG. 5. The calibrate routine samples cuff pressure once every second and displays the resulting value on display 140. A mercury manometer and syringe can be connected to cuff 114 and/or pressure transducer 106 during this time to calibrate system 100. Additionally, tape recorder 112 may be turned on during this time to permit testing of analog signal processor 104 by exposing ECG electrodes 110 and K-sound transducer 108 to known conditions and subsequently analyzing the signals recorded by the tape recorder. Digital processor 102 may automatically transmit the results of measurements performed during execution of the calibrate routine to output connector 160 in digital form to allow real time evaluation of the information by an external peripheral device. The calibrate routine has great utility during initial factory calibration of system 100 or at any time the accuracy of the system is to be validated.

Once calibrate routine 214 is entered, digital processor 102 activates tape recorder 112 (block 216) and begins executing a loop comprising blocks 218-224. A one second delay is timed (block 218), and digital signals corresponding to the outputs of pressure transducer 106, K-sound transducer 108 and ECG electrodes 110 are acquired (by controlling ADC 172 in a conventional fashion) and stored in RAM 132 (block 220). The acquired data may be displayed on display 140 (block 222) and transmitted via connector 160. It is then determined whether "START" button 154(d) has been depressed (decision block 224). If "START" button 154(d) has been depressed, recorder 112 is turned off (block 226) and the calibration routine 212 is terminated. However, if "START" button 154(d) has not yet been depressed, blocks 218-222 are executed again to obtain another measurement. Blocks 218-224 are repeatedly performed until the "START" button 154(d) is finally depressed.

Referring once again to FIG. 5, after "START" button 154(d) has been depressed by the user (block 212 or 224), system 100 enters the "wait" state (i) (by setting a flag in a conventional manner) (block 228). Digital processor 102 then begins executing a continuous loop comprising blocks 230-246.

Decision block 230 tests whether the "STOP" switch 154(b) has been depressed. If "STOP" switch 154(b) has not been depressed (indicating that on-going measurements are to be conducted), decision block 232 tests whether the user desires system 100 to operate in the "manual" or the "automatic" mode (block 232) by determining the position of "auto/manual" switch 154(e). If system 100 is operating in the manual mode, cuff cycles are initiated manually by depressing "START" switch 154(d) (block 240) (the manual mode is suitable for conducting measurements one at a time at a physician's office or for initially checking the operation of the system after it has been connected to the subject).

If system 100 is operating in the "automatic" mode, it is determined whether an intercuff cycle interval timer has timed out (decision block 234). If the interval has timed out (initialization block 208 sees to it that this will initially be the case), decision block 236 tests whether system 100 is in the "rapid deflate" state (v) or in the "wait" state (i). If system 100 is in the "wait" or "rapid deflate" state, the inter-cuff cycle interval timer 238 is reset (block 238) (the inter-cuff cycle interval timer is, in fact, "reset" to either a predetermined or a random value depending upon the position of "random/fixed" switch 154(g), as will be further explained in connection with FIG. 7). A cuff cycle is performed by sequentially entering the "inflate" state (ii), (block 242), the "hold" state (iii) (block 244) and the "linearly deflate" and "rapid deflate" states (iv and v) (the combination of which is represented by block 246). At the conclusion of the cuff cycle, system 100 enters the "wait" state (i) and control is transferred back to decision block 230.

If system 100 is operating in the "manual" mode (decision 232), blocks 234-238 are bypassed and the depression of the "START" button 154(d) is used to initiate a cuff cycle (decision block 240). Decision block 234 prevents a cuff cycle from beginning in the automatic mode before the proper time, while decision block 236 prevents a second cuff cycle from beginning before a first cuff cycle has ended.

The loop comprising blocks 230-246 is continually executed after the initial depression of the "START" button 154(d) (decision block 212) until the user depresses the "STOP" button 154(b) (decision block 230). If the "STOP" button is depressed, air valve 120 is opened (block 248) to deflate cuff 114, and a loop comprising decision blocks 250 and 252 are repeatedly performed to await depression of either the "DUMP DATA" button 154(c) or the "START" button 154(d), respectively. Preferably (although not indicated in the Figures), depression of "STOP" button 154 (b) at any time will cause digital processor 102 to execute blocks 248-252 (so that in an emergency, a cuff cycle can be aborted at will).

If the "DUMP DATA" button 154(c) is depressed (decision block 250), the user has requested system 100 to transmit the results of measurements serially via output line 156 to an external peripheral device (e.g. a printer, a CRT display, a computer, etc.). System 100 executes block 254 to remove information stored in RAM 132 (preferably, this data is stored in the RAM in a predetermined manner with appropriate header information to make it suitable for direct print-out by a standard ASCII printer or display), convert it from parallel binary to serial ASCII format, add appropriate protocol information, and transmit the serial information to output connector 160.

The preferred embodiment transmits information to output connector 160 using RS-232C serial communication protocol and conventions to provide compatibility with existing peripheral devices. However, it will be understood that any conventional serial or parallel digital communication convention could be used instead. For instance, a conventional modem could be substituted for output connector 160 to permit transmission of information via conventional telephone lines. Alternatively, transmission of information from system 100 to an external peripheral device could be accomplished across free space via radio, audio or ultrasonic frequency transmission, infrared or optical light transmission paths, etc. Requirements of particular users may largely determine the type of communications used by system 100.

If a standard ASCII printer or CRT display is connected to output connector 160 and the "DUMP DATA" button 154(c) is depressed, the printer (display) preferably will display information directly in a useful format which can be easily interpreted by the physician.

The display includes sample number, the time the sample was taken (in real time), systolic and diastolic blood pressure and heart rate. Other information (such as mean blood pressure for each sample, mean blood pressure for a plurality of samples, date, etc.) can also be displayed if desired. An example of such a display in accordance with the presently preferred exemplary embodiment of the present invention is shown in Table I below:

TABLE I

| SAMPLE NO. | TIME | SYS | DIA | HR |
|---|---|---|---|---|
| 1 | 18:15 | 125 | 074 | 076 |
| 2 | 18:39 | 129 | 078 | 079 |
| 3 | 18:45 | 135 | 080 | 078 |
| 4 | 19:18 | 138 | 084 | 086 |
| 5 | 19:27 | 142 | 092 | 097 |
| 6 | 19:35 | 133 | 086 | 091 |
| 7 | 19:45 | 128 | 075 | 084 |
| 8 | 20:18 | 123 | 073 | 080 |

After data has been output upon command of the user (block 254), control is transferred back to the loop comprising blocks 248-252. If desired, data may be retransmitted to another external peripheral device or to the same peripheral device (if transmission errors occurred previously) by depressing the "DUMP DATA" button 154(c) once again (block 250). Alternatively, the "START" button 154(d) may be depressed again to restart the sequencing of the loop comprised of blocks 230-246.

Figure 7:
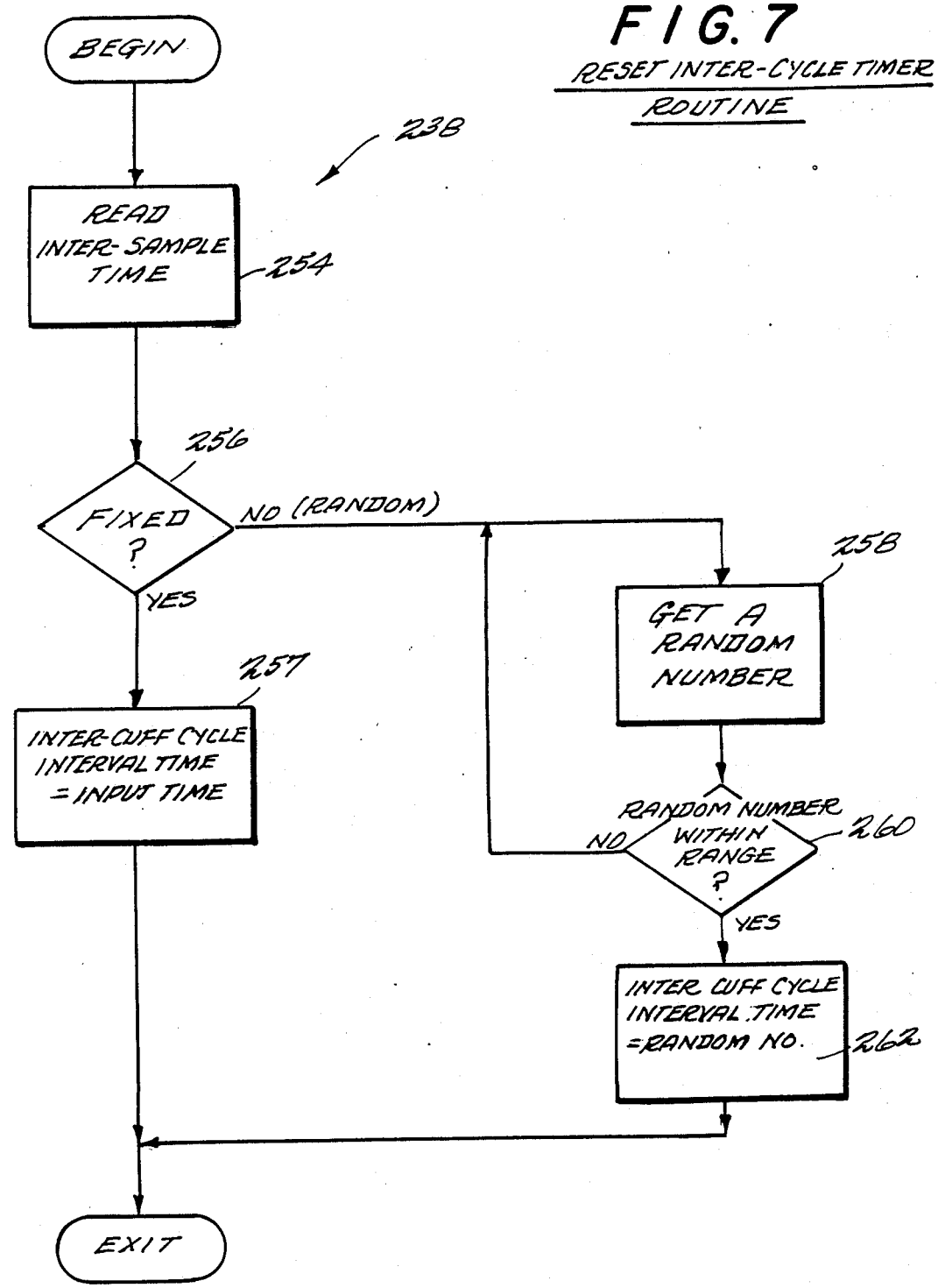
FIG. 7 is a detailed flow chart of the "Reset Inter-Cuff Cycle Interval Timer" block shown in FIG. 5.

FIG. 7 is a detailed flow chart of the "Reset Inter-Cuff Cycle Interval Timer" block 238. In the preferred embodiment, just prior to the beginning of each cuff cycle, the time interval until the next cuff cycle is to be begun is set by block 238 (although the preferred embodiment times inter-cuff cycle intervals from the beginning of one cuff cycle to the beginning of the next cuff cycle, it will, of course, be understood that this interval could be timed from the end of one cuff cycle to the beginning of the next, the end of one cuff cycle to the end of the next, etc.) The setting of the "Inter-Sample Time" "DIP" switches 146 is read (either directly from the switch itself via MUX 162 in a conventional manner, or, if the setting of the switch has already been stored in RAM 132 by initialization block 208, from a predetermined location in the RAM).

The setting of "Inter-Sample Time" switch 146 is interpreted by system 100 in one of two different ways depending upon the position of "random/fixed" switch 154(g). If the user has selected the inter-sample time (i.e. the time between cuff cycles) to be fixed, the setting of switch 146 is used by system 100 as a fixed intersample time interval. However, if the user has selected (by the position of "random/fixed" switch 154(g)) the "random" mode of operation, system 100 selects a random inter-sample time $\tau$ from the range of values $0 < \tau \leq$ setting of inter-sample time switch 146 (of course, this range may be modified to require the inter-sample time to be at least two or more minutes to avoid excessively repetitious cuff cycles). Alternatively, means can be provided to permit a user to input both lower and upper limits of the range of the random inter-sample time.

If switch 154(g) is in the "fixed" position, the inter-cuff cycle interval timer is set to the setting of switch 146 (block 257). If, however, the "random" mode has been selected, system 100 obtains a random number from a random number generator (block 258). The random number may be obtained from a hardware or software random number generator conventional in design.

If the random number produced by the random number generator is within the programmed intersample timer range (decision block 260), the random number is used to set the inter—cuff—a software random number generating procedure is used in the preferred embodiment. Numbers produced by the software random number procedure are psuedo-random because the procedure is itself fixed rather than random. As is well known, however, such conventional procedures produced a series of numbers which pass extensive tests for randomness. The software procedure used may be any one of the many conventional procedures (e.g., a congruential, shift-register or combining generative for generating pseudo-random numbers). See, e.g., Ralston et al, *Encyclopedia of Computer Science and Engineering*, pp. 1260–64 (Van Nostrand Reinhold Co. 1983); Knuth, D., *The Art of Computer Programming* 2 (*Seminumerical Algorithms*) (Addison-Wesley 1981); Marsaglia, G., "The Structure of Linear Congruential Sequences," reprinted in Zaremba, S. K., *Applications of Number Theory to Numerical Analysis* (Academic Press 1972); and Golomb, S. W., *Shift Register Sequences* (Holden Day 1967) cycle interval timer (block 262). If the obtained random number is not within the desired intersample time interval, block 258 is executed once again to obtain a new random number (block 258 is repeatedly executed until a random number within the present range is obtained).

Subjects often consciously or subconsciously change their blood pressure and heart rate just before the onset of a blood pressure measurement if they are aware the measurement is to be taken. Commonly, for instance, a patient's blood pressure will be abnormally elevated during clinical blood pressure tests due to nervousness. Some patients actually mentally force themselves to relax or otherwise abnormally decrease their blood pressure just prior to and during a blood pressure test to avoid being diagnosed as hypertensive. However, patients typically require some time to affect their blood pressure and heart rate, and therefore cannot do so if the measurement takes them by surprise. By using a random inter-sample time interval, the patient cannot predict in advance when a cuff cycle will begin and therefore cannot alter his or her blood pressure and/or heart rate to affect the measurement. Measurements performed unexpectedly, automatically and swiftly (as in accordance with the present invention) produce a far more accurate indication of the true cardiovascular parameters of a patient. Moreover, random intersample time intervals are important and helpful to the proper diagnosis of certain kinds of cardiovascular problems.

Although a true (pseudo-random number generation process is used in the preferred embodiment to produce a random inter-cuff cycle interval value, all that is required is that the length of the inter-sample time interval cannot be predicted in advance by the patient (i.e., the interval must be essentially arbitrarily chosen). Therefore, for example, it might suffice to store a plurality of unrelated inter-sample time interval values in EPROM 130 and sequentially read these values to obtain a "random" inter-sample time. Alternatively, a mathematical formula might be used to calculate the next inter-sample time from one or more previous inter-sample times, or some other changing parameter could be used to derive the next inter-sample time (provided the derived inter-sample time is not easily predictable by the patient). The term "random value" as used in the appended claims is intended to include not only a true or pseudo-random value, but also a value selected so that it cannot be easily predicted by the patient.

Figure 8A:
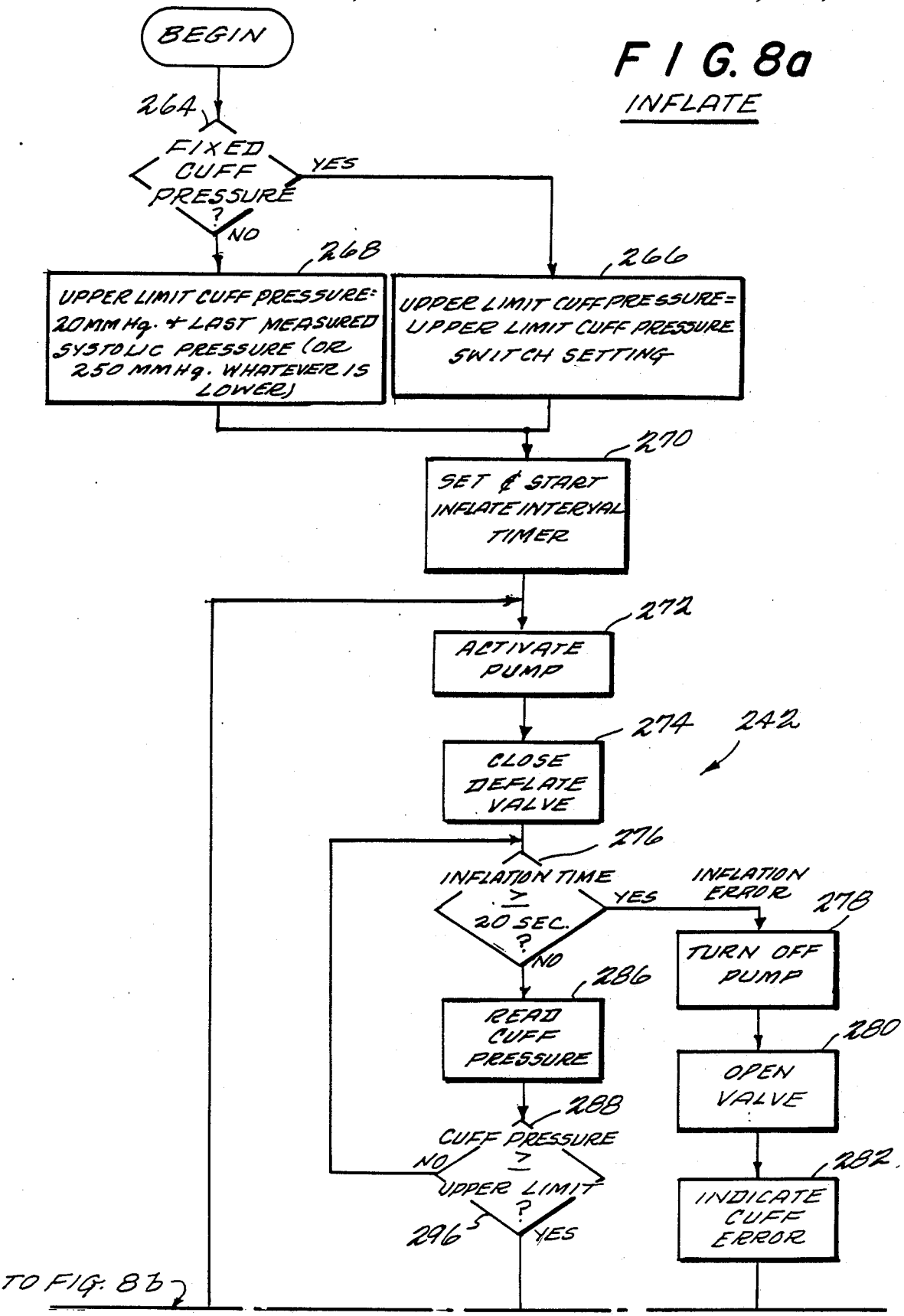
FIGS. 8(A) and 8(B) are flow charts of the "Inflate Cuff" block shown in FIG. 5.
Figure 8B:
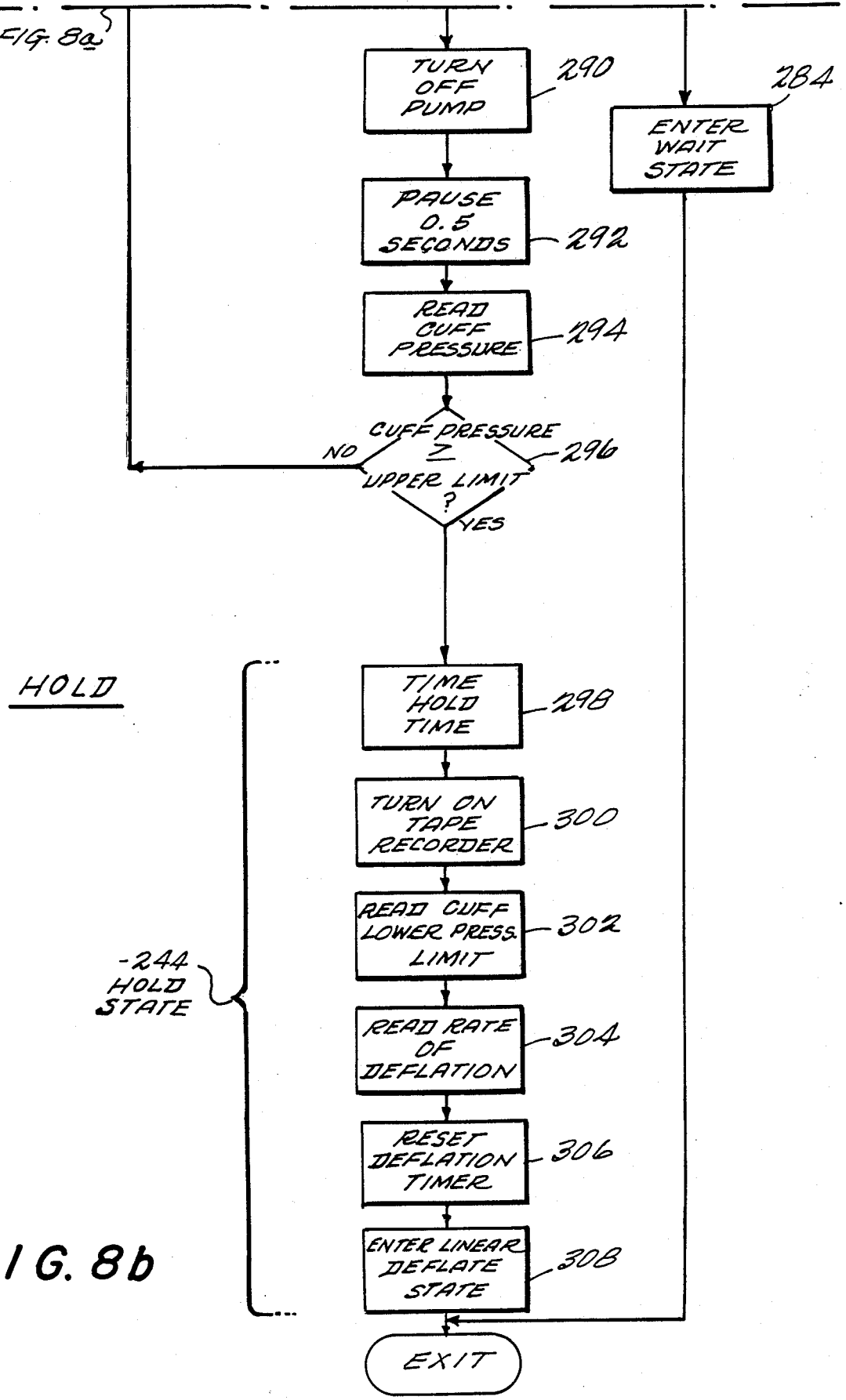

FIGS. 8(A) and 8(B) are flow charts of inflate block 242 and hold block 244 shown in FIG. 5. The steps shown in FIG. 8 are performed to begin the next cuff cycle. If the "FIXED/DYNAMIC" switch 754(f) is in the "fixed" position (block 264), the setting of "Upper Limit Cuff Pressure" switch 152 is stored in a register later to be used as the upper limit cuff pressure value (block 266). If, however, the cuff pressure is to be set dynamically, system 100 determines the upper limit cuff pressure from one or more previously measured systolic pressure values of the patient (block 268). In this way, the preferred embodiment avoids exposing the patient to discomfort due to excessive cuff pressure. More particular, block 268 in the preferred embodiment stores the sum of the last measured systolic pressure of the patient and 20 mmHg (or a total value of 250 mmHg, whichever is lower) in the register to be later used to determine upper limit cuff pressure. It will be understood, of course, that a plurality of previously measured systolic pressure values could be averaged or otherwise combined to obtain the dynamic upper limit cuff pressure value, the upper limit value could be derived from diastolic pressure, etc. The upper pressure limit value need only be sufficiently above the patient's systolic pressure to permit accurate systolic pressure measurements to be obtained, and should be low enough to avoid excessive discomfort to the patient.

To begin a cuff cycle, an inflation interval timer is initialized (e.g. reset) (block 270), pump 118 is activated (block 272), and air valve 120 is closed (block 274). If system 100 operates in the "inflate" state (ii) for more than a predetermined period of time (e.g. 20 seconds), system 100 aborts the present cuff cycle because it is unable to sufficiently inflate cuff 114 (i.e. the cuff has a air leak, pump 118 or air valve 120 has malfunctioned, the cuff is improperly placed on the patient's arm, pressure transducer 106 or analog signal processor 104 has malfunctioned, etc.) If an inflation error occurs, pump 118 is turned off (block 278) and air valve 120 is opened (block 280), LCD 140 is controlled to indicate a cuff inflation error (block 282), and system 100 enters the "wait" state (i) to await the onset of the next cuff cycle (to "try again") (block 284).

If the inflation timer has timed less than the predetermined time duration, the pressure of cuff 114 is measured by controlling analog signal processor 104 to present the digitized value of the signal level output of pressure transducer 106 to digital signal processor 102 (block 286). The measured cuff pressure is compared with the upper limit cuff pressure previously selected by one of blocks 266 and 268 (block 288). If the actual cuff pressure is less than the desired limit, control is transferred back to decision block 276. The loop comprising blocks 276, 286 and 288 is continuously executed until either too much time has gone by (indicating an inflation error) or the actual cuff pressure finally reaches the desired upper limit cuff pressure. Once the pressure within cuff 114 reaches the desired value (decision block 288), pump 118 is turned off (block 290), a pause of 0.5 seconds occurs to permit cuff pressure to stabilize (block 292), the actual cuff pressure is read once again (block 294) after a slight delay (block 294), and the actual cuff pressure is once again compared with the desired upper limit cuff pressure (decision block 296). If the cuff pressure has fallen, control is transferred back to block 272 to once again activate pump 118 to try to inflate cuff 114 to the desired level. In this way, the actual pressure within cuff 114 reaches the desired level before measurements are performed. Of course, blocks 292-296 can be eliminated if cuff pressure does not tend to fall after reaching the desired pressure.

The "inflate" state (ii) is implemented by blocks 264-296. After the "inflate" state is finished, system 100 enters the "hold" state (iii), performed by blocks 298-308. After a predetermined time (which is fixed at 1.0 seconds in the preferred embodiment, but may be programmable if desired) has elapsed (block 298), to permit pneumatic ringing and other disturbances within the cuff to subside, tape recorder 112 is turned on (block 300) and the values controlling the rate of linear deflation of the "linear deflate" step (iv) are preset in accordance with user-programmed parameters (blocks 302-306). More particular, the cuff lower pressure limit is read from the "Lower Limit Cuff Pressure" switch 150, the rate of deflation is obtained from the setting of the "rate of deflation" switch 148 (the setting of which may be varied in the preferred embodiment from 1 mmHg/sec to 10 mmHg/sec), and a deflation timer is reset (block 306). After the "hold" state is completed the "linear deflate" state (iv) is entered (block 308).

Figure 9:
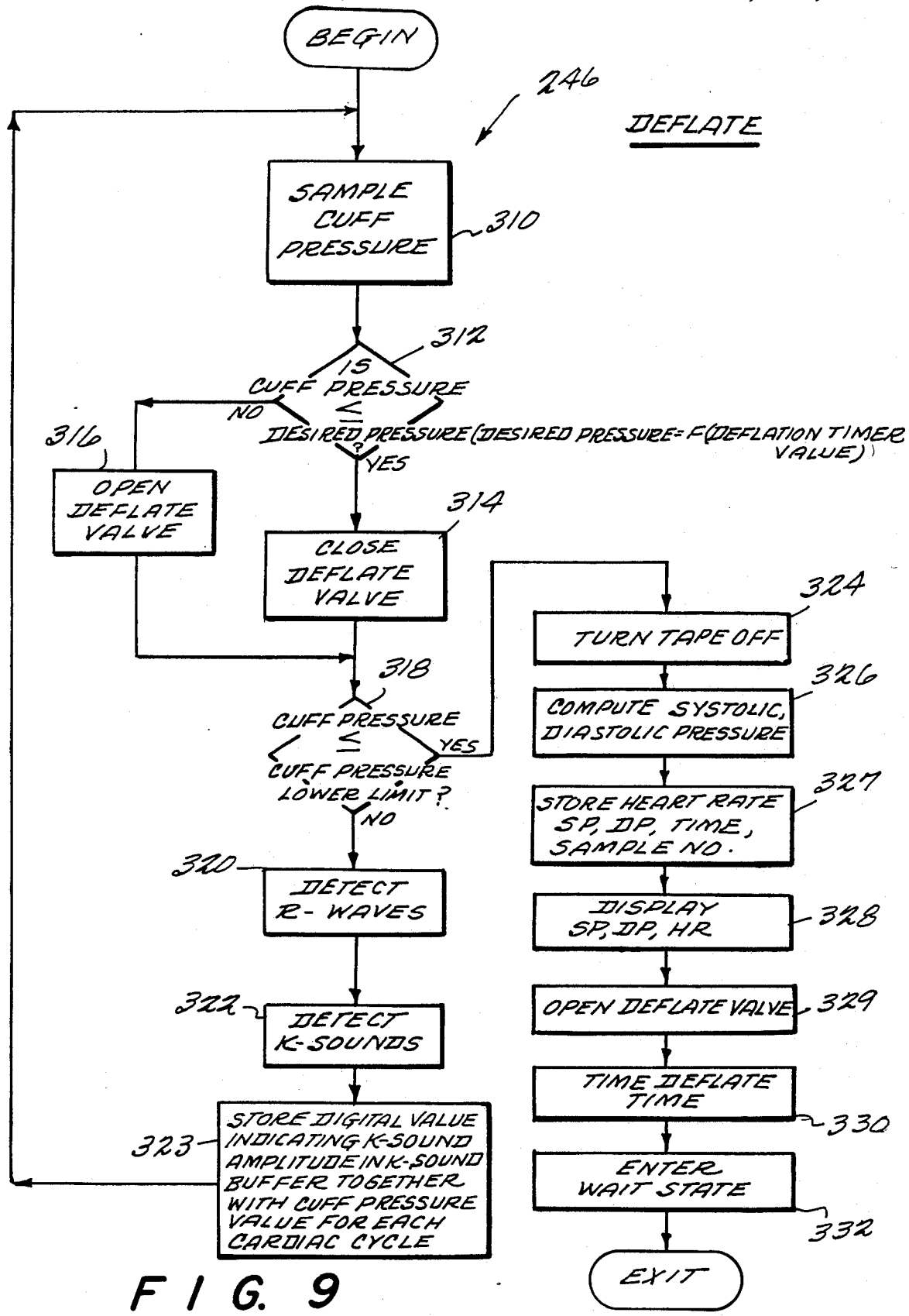
FIG. 9 is a flow chart of the "Deflate Cuff" block shown in FIG. 5.

FIG. 9 is a detailed flow chart of the "deflate" block 246 shown in FIG. 5. Blocks 310-322 of FIG. 9 perform the "linear deflate" state (iv), while blocks 324-332 comprise the "rapid deflate" state (v).

It is during the "linear deflate" state (iv) that system 100 measures blood pressure and heart rate. As is shown in FIG. 3, the rate of deflation of cuff 114 with time during the "linear deflate" state (iv) is linear to make measurements more repeatable and accurate. Linearity in the preferred embodiment is better than ±1 mmHg to achieve fixed resolution which does not change during the cuff cycle. During the "linear deflate" state (iv), system 100 periodically monitors the pressure of cuff 114 and compares it with a predetermined stored software linear deflation profile to ensure that actual cuff pressure tracks the software profile. Cuff pressure is sampled (block 310) and compared with the desired cuff pressure value in accordance with the software profile (decision block 312). The desired cuff pressure value in accordance with the software profile may be calculated for each point in time during the "linear deflate" state (iv) by simply multiplying the value of the deflation timer by the rate of deflation selected by switch 148 and subtracting the product from the upper limit cuff pressure. Alternatively, to save computation time, initialization routine 208 may pre-calculate the desired cuff pressure profile for a predetermined plurality of values of the deflation timer to increase the processor time available for real-time calculation and analysis of data and to minimize the number of openings and closings of air value 120 during the "linear deflate" state (iv) (consistent, of course, with desired true linearity of cuff deflation). Special non-linear profiles (such as logarithmic, exponential, or periodic profiles) could be used instead of the linear profile if desired to perform special tests on a repeatable basis.

If the measured cuff pressure falls below the desired cuff pressure determined from the software profile, air valve 120 is closed (block 314). If, however, the measured cuff pressure is greater than the profile value for the present value of the deflation timer, air valve 120 is opened (block 316). It will be understood that a desired degree of hysteresis may be incorporated into either the software profile or decision block 312 to prevent undue wear of air valve 120 (consistent with accuracy requirements). Additionally, a short period of measurement dead time is preferably observed immediately after opening and closing of valve 120 to permit pneumatic ringing to subside (e.g., the valve opening and closing may be synchronized with R-waves obtained from ECG electrodes 110 to ensure ringing subsides by the time a K-sound occurs). If the cuff pressure is above the lower limit cuff pressure (decision block 318), Korotkoff sounds and heart rate are detected (block 320 and 322) and control is returned to block 310 for another execution of the loop comprising blocks 310-322.

FIGS. 10(A) and 10(G) show signals used in accordance with the present invention to detect the R-wave (QRS segment) of the electrocardiogram (ECG) waveform derived from ECG electrodes 110 (block 320). In accordance with the present invention, a few ECG cycles (FIG. 10(A)) are initially sampled to determine the peak amplitude of the signal. Peak signal amplitude may be determined based upon a running average of a plurality of previously-detected R-waves, statistical averaging of stored amplitudes of R-waves of the patient detected during one or more previous cuff cycles or during the "wait" state (i), etc. Digital signal processor 102 considers an R-wave to arrive at the instant the peak of an R-wave waveform occurs to avoid error due to variations in signal waveform.

System 100 establishes an R-wave threshold equal to approximately 50% of the peak R-wave signal based upon the amplitude of a few ECG cycles. Whenever the received R-wave has an amplitude which exceeds this threshold value, a signal RTHRSH (FIG. 10(e)) is produced. An R-wave is assumed to have occurred when the slope of the R-wave changes from positive to negative while the amplitude of the wave is still above the established threshold. The slope change of the waveform is detected in a conventional manner and triggers a falling edge on a signal SLOPE (FIG. 10(d)). When a falling edge of SLOPE occurs while the signal RTHRSH is present, a signal R-FLAG (FIG. 10(g)) is produced and an R-wave timer internal to digital processor 102 begins timing a predetermined time period (e.g. 400 ms in the preferred embodiment) (FIG. 10(f)). During the interval timed by the R-wave timer, the ECG signal derived from electrodes 110 is ignored since no additional R-waves should be present during this time (it is assumed that heart rate cannot exceed a predetermined rate). The R-FLAG signal continues to be produced until the R-wave timer times out, at which time the R-FLAG signal is deasserted. The R-FLAG signal serves as a synchronization (gating) signal to detect Korotkoff sounds.

Heart rate is calculated by measuring the average interval between a predetermined number (suitably 10) of received R-waves. The heart rate information may be derived from the leading edge of R-FLAG signal if desired. Of course, heart rate could be calculated from received Korotkoff sounds or sensed pressure pulsations of cuff 114 if desired.

FIGS. 11(a)-11(i) show the waveforms used by the preferred embodiment to detect the occurrence of Korotkoff sounds. FIG. 11(a) is a series of pulses (which represents the occurrence of the R-wave of the ECG). As will be recalled, the signal R-FLAG is produced each time an R-wave is detected (see FIG. 11(e)). As soon as an R-wave is detected, a signal K-DELAY (shown in FIG. 11(b)) is produced for a predetermined period of time. The duration of K-delay is 100 ms in the preferred embodiment, but the duration may be programmable if desired. When this predetermined delay has elapsed, a signal "K-WINDOW" is produced (FIG. 11(c)). It is during the presence of the K-WINDOW signal that system 100 is sensitive to Korotkoff sounds detected by K-sounds transducer 108.

The signal K-WINDOW may be produced for a predetermined period of time (e.g. 200 ms) or it may be asserted for a duration dependent upon a variable factor (such as heart rate). Because system 100 is sensitive to K-sounds only during the time the signal K-WINDOW is present, noise and other artifacts have less chance to affect pressure measurements.

A K-sound threshold level is established to help reject artifacts in the sensed K-sound signal. If no threshold has been previously established, an arbitrary initial threshold value of 0.25 volts is used in the preferred embodiment. After a cuff cycle has occurred, a new threshold value is calculated by averaging all of the peak values of the K-sound signals obtained during the cycle and setting the threshold to ½ of this average value (a running average during a cuff cycle can be used to obtain this average value or alternatively, statistical averaging of values from one or a plurality of previously cuff cycles could be used). For a K-sound to be detected, it must rise above this K-sound threshold value.

Upon detection of a K-sound signal which rises above the threshold value, a signal KS FLAG is briefly produced (FIG. 11(d)). Another signal K-FLAG is then set for the remainder of the cardiac cycle if the leading edge of which is within the WINDOW of time established by K-WINDOW, (FIG. 11(g)). The function of the signal K-FLAG is to prevent system 100 from responding to any additional K-sounds until the next cardiac cycle occurs (as only one legitimate Korotkoff sound is produced for any given cardiac systole). The signal K-FLAG continues to be produced until the time the next R-wave is detected.

If no Korotkoff sound has been detected by the time the K-WINDOW signal drops to logic level 0, a signal K-MISS is produced to indicate a missed Korotkoff sound. System 100 determines if Korotkoff sounds are detected in consecutive cardiac cycles and keeps track of the number of missed Korotkoff sounds that occur within the cuff cycle. If fewer than a predetermined number of consecutive Korotkoff sounds (suitably four) are detected in a given cuff cycle, the entire cuff cycle measurement is aborted. Also, if more than a predetermined number (e.g. three) of Korotkoff sounds are missed before consecutive Korotkoff sounds are detected in a cuff cycle, the Korotkoff sounds detected before the point the consecutive Korotkoff sounds begin are ignored and treated as false Korotkoff sounds.

Figure 10:
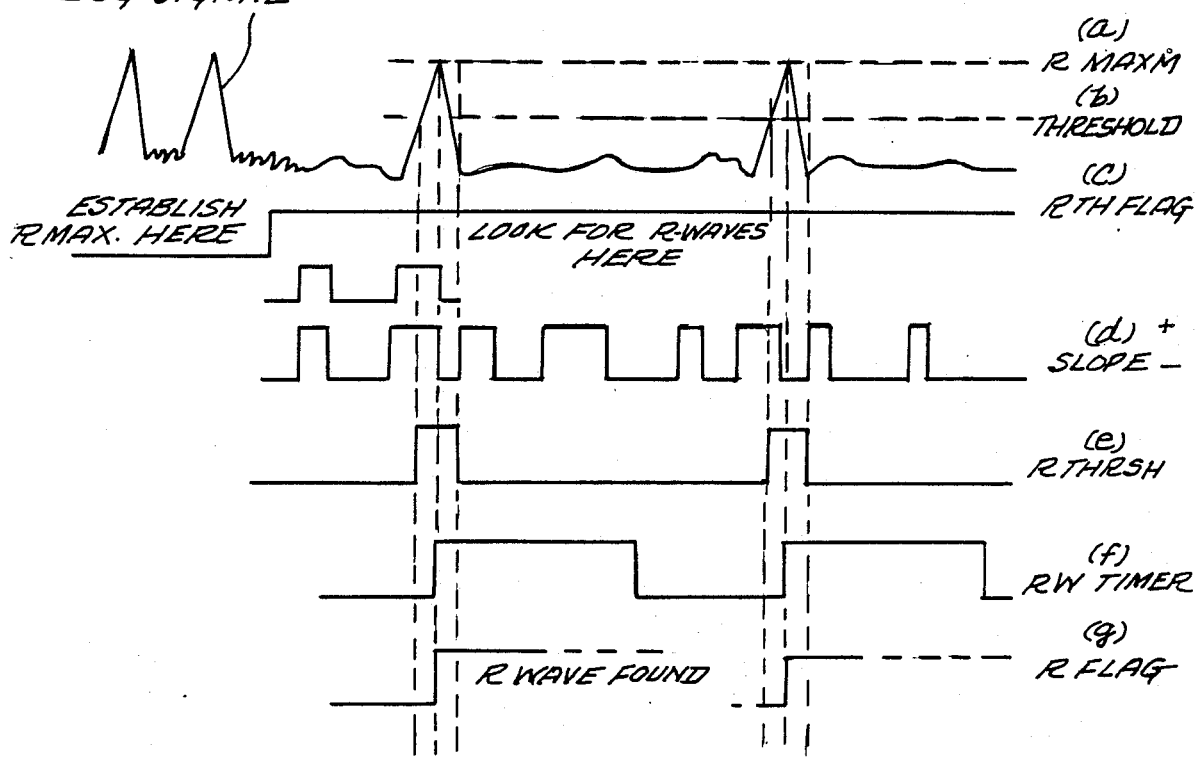
FIG. 10 is a graphical illustration of the detection of R-waves in accordance with the present invention.
Figure 11:
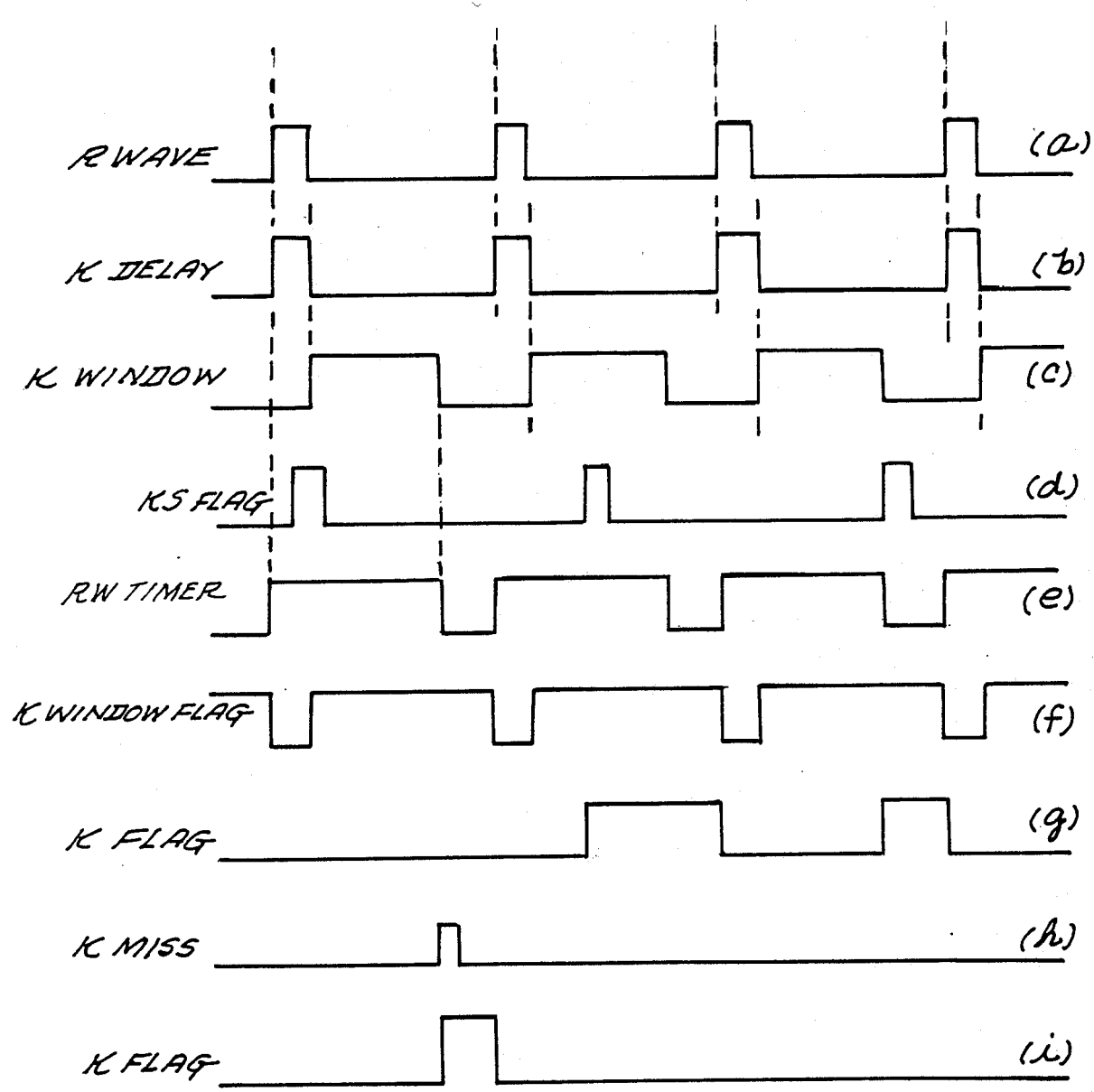
FIGS. 11(a)-11(i) are timing diagrams of signals produced by the system shown in FIG. 1 to reliably detect Korotkoff sounds.

The signals depicted in FIGS. 10 and 11 could be produced by discrete digital logic elements or even analog signal processing components. However, in the preferred embodiment, the signal processing described in connection with FIGS. 10 and 11 is performed by digital processor 102 in the digital domain under software control.

Referring to FIG. 9 once again, the pressure within cuff 114 will fall below the lower limit cuff pressure set by switch 150 (decision block 318) after a time. When this occurs, no further useful measurements may be obtained (since the cuff pressure has fallen below the patient's diastolic pressure), and the "rapid deflate" state (v) is entered to relieve cuff pressure as rapidly as possible to eliminate further patient discomfort. Tape recorder 112 is turned off (block 324), and the patient's heart rate is computed from the average time interval between the leading edges of the first 10 R-waves of the ECG signals detected during the time cuff 114 was linearly deflated (block 326). Systolic and diastolic pressure values and heart rate values for the last cuff cycle are stored in RAM 132 together with the sample number (obtained by incrementing a sample number counter) and the real time (obtained from the real time timer discussed previously) (block 327), and systolic and diastolic pressures plus heart rate are displayed on LCD 140 (block 328) to facilitate biofeedback or other applications wherein immediate data indication is desired (other calculations can be performed as well if desired). Air valve 120 is opened (block 329) for at least a predetermined period of time (as timed by block 330) to insure complete deflation of cuff 114. System 100 then enters into the "wait" state (i) to await the onset of the next cuff cycle (block 332).

Figure 12:
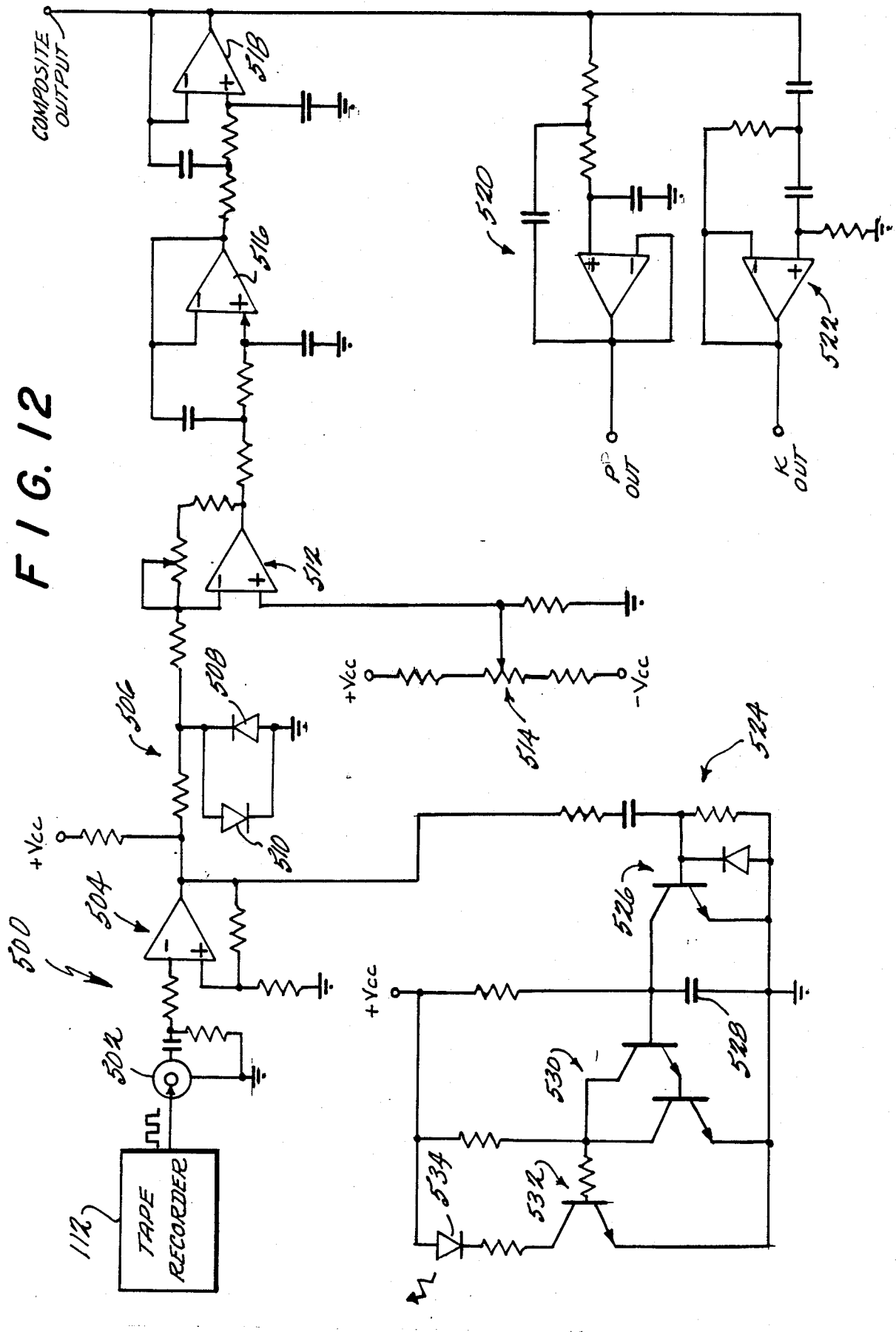
FIG. 12 is a schematic diagram of a suitable decoder for decoding information recorded on the tape recorder shown in FIG. 1.

FIG. 12 is a schematic diagram of a suitable decoder 500 for use in extracting information from the audio output of the tape recorder during playback, while FIG. 13 is a graphical illustration of the information obtainable from decoder 500. To obtain the information stored on the tape of recorder 112, the audio output of the tape recorder is connected to input jack 502 of decoder 500 (or the tape is removed from recorder 112 and placed into a separate tape player and the recorder (player) is placed into its playback mode. Playback may be at a speed two to four times faster than the record speed since the ratio of on-time to off-time of the recorded signals does not change with tape speed. The on-time to off-time ratio of the playback signal contains the useful measurement information to be extracted and displayed.

The output of tape recorder 112 is amplified by an amplifier stage 504. A limiter 506 comprising diodes 508 and 510 prevents excessive signal levels from introducing distortion into the output of decoder 500. A comparator 512 having an adjustable threshold compare the amplitude of the signal at the output of limiter 506 with a fixed reference signal produced by a reference voltage source 514. Whenever the amplitude of the modulated envelope exceeds the output of reference source 514, comparator 512 produces a logic level zero output. Likewise, whenever the level of the modulated envelope appearing at the output of limiter 506 is less than the output of reference voltage source 514, comparator 512 produces a logic level one output. In this way, the carrier component of the modulated envelope is eliminated from the composite K-sound and pressure signal (so that the output of comparator 512 is a replica of the output of summing amplifier 196 of analog signal processor 104 of system 100). The output of comparator 512 is amplified by cascaded amplifiers 516 and 518 (which also filter out extraneous noise introduced by tape recorder 112 itself and by earlier signal processing stages).

The output of amplifier stage 518 is a nearly exact replica of the output of summing amplifier 196 of system 100, and may be displayed on an oscilloscope or otherwise analyzed in a conventional fashion. A low-pass filter 520 having a suitable cut-off frequency removes the pressure signal from the composite output produced by amplifier 518 (the pressure waveform, of course, has a relatively low frequency), while a high-pass filter 522 extracts the K-sounds from the composite output. Hence, the output of low-pass filter 520 is a replica of the output of amplifier 168 of analog signal processor 104, while the output of high-pass filter 522 is a replica of the output of switch 198 of the analog signal processor.

An example of the output waveforms produced by filters 520 and 522 are graphically shown in FIG. 13. These signals may be plotted by a conventional chart recorder or displayed on an oscilloscope to obtain a display of Korotkoff sounds and cuff pressure versus time from which, of course, heart rate and blood pressure may be determined in a conventional manner.

Decoder 500 also includes a circuit 524 which indicates the presence of signal levels above a predetermined level being played back by tape recorder 112. The output of amplifier 504 is limited and amplified by a transistor amplifier stage 526, filtered by a capacitor 528, further amplified by a Darlington-configured amplifier stage 530, and used to drive the base of a switching transistor 532. Switching transistor 532 turns on a light-emitting diode (LED) 534 when sufficient base drive is applied to the switching transistor, thereby indicating to a user that useful signal information is being played back by tape recorder 112. If desired, the output of amplifier stage 530 may be used to automatically control the gain of one or more of amplifiers 512–518 to minimize fluctuations in the amplitude of the output of amplifier 518 as the playback level of tape recorder 112 varies.

DESCRIPTION OF END CYCLE ANALYSIS

System 100 as described could simply attempt to determine in real time which Korotkoff sound measured during a cuff cycle corresponds to the systolic blood pressure of the patient and which measured Korotkoff sound corresponds to the diastolic blood pressure of the patient. As has been described, however, this approach can and frequently does lead to erroneous pressure determinations because the measuring system has no way of determining whether the signals appearing on the Korotkoff sound channel (within the K-sound time window) are produced by real Korotkoff sounds associated with the Korotkoff sound envelope occurring between systolic and diastolic cuff pressure points, or whether the signals are produced by spurious noise and/or artifacts having frequency characteristics similar to those of real Korotkoff sounds.

It is possible to establish a dynamic Korotkoff sound threshold level based upon the amplitudes of the Korotkoff sounds measured during one or more previous cuff cycles, and to use this dynamic threshold to help eliminate signals not produced by Korotkoff sounds (for example, any signals present on the Korotkoff sound channel which lie below this dynamic threshold level can be ignored). Unfortunately, the Korotkoff sound amplitude and/or waveform of a subject can and often does change due to effects that are not presently entirely understood. If a subject's Kootkoff sound profile should suddenly change drastically from one cuff cycle to the next, or worse yet, within the same cuff cycle, a system employing real-time K-sound analysis techniques cannot compensate for the changes in the K-sound envelope profile, and therefore may determine systolic and diastolic blood pressure erroneously.

The preferred embodiment of the present invention employs an "end-cycle analysis technique" which helps reduce or eliminate entirely the problems of erroneous determination of Korotkoff sounds and thus greatly increases the accuracy of the system. The end-cycle analysis technique, as the terminology implies, acquires cuff pressure and Korotkoff sound information in real time for each cardiac cycle of the cuff deflation process and stores this information in a buffer area allocated in random access memory 132. The K-sound analysis and pressure determination algorithm is invoked at the *end* of the cuff deflation cycle (i.e., after the pressure in cuff 114 falls below the diastolic blood pressure of the subject and during the time system 100 is in the "rapid deflate" state (v)).

The buffer area of RAM 132 is first scanned and system 100 processes the K-sound data for all cardiac cycles that occurred during cuff deflation. The preferred embodiment first determines when maximum K-sound activity occurred by locating the five consecutive K-sounds having the greatest average amplitude. The middle cardiac cycle and corresponding K-sound of these five consecutive heart beats is assumed to represent the center of maximum Korotkoff sound activity during the cuff cycle. This largest average amplitude value also represents the overall K-sound envelope magnitude, and is used by system 100 to determine whether the gain of K-sound amplifier 174 should be dynamically changed.

Next, system 100 performs two other averaging functions. First, it determines the average of the amplitudes of *all* Korotkoff sound signals falling within the K-sound window K WINDOW for each cardiac cycle that occurred during linear cuff deflation. This overall average value represents a normalized K-sound amplitude limit. Any Korotkoff sounds having an amplitude above this limit are not considered likely candidates for corresponding to either systolic or diastolic pressure. Secondly, all K-sound signals within the K-sound time window (K WINDOW) having amplitudes below this normalized limit are averaged to obtain a lower-level mean value. This lower-level mean value represents the normalized average noise and artifact level during cuff deflation. K-sounds with amplitudes below this lower-level mean value are also not considered for pressure determination. A value equal to half the difference between the overall average and the lower level mean value is established as a K-sound threshold.

Starting with the cardiac cycle corresponding to the center of maximum K-sound activity, the preferred embodiment scans the buffer area in two directions (forward and backward), evaluating each stored K-sound level with respect to the K-sound threshold. When scanning toward the beginning of the cuff deflation cycle (i.e. backward in time from the center of K-sound activity), the preferred embodiment searches for the latest K-sound in time occurring prior to the center of maximum K-sound activity that falls below the K-sound threshold. When this latest K-sound is found, the preferred embodiment evaluates the two immediately preceding K-sound levels in time to determine whether they also lie below the K-sound threshold. If these two earlier values also lie below the threshold and the cuff pressure corresponding to these is on "linear track" (i.e., close to an expected result dictated by the software linear deflation model), then the latest K-sound (occurring before maximum K-sound activity) that is below the K-sound threshold is selected as the K-sound corresponding to the systolic blood pressure of the patient, and the cuff pressure associated with that cardiac cycle (also stored in the buffer area) is taken as systolic blood pressure. However, if the cuff pressure corresponding to these two earlier K-sounds is not on a "linear track", the preferred embodiment assumes an auscultatory gap has occurred and continues to scan the buffer area for an earlier K-sound level which lies below the K-sound threshold. The same procedure is followed to scan the information stored in the buffer area corresponding to cardiac cycles which occurred near the end of the cuff cycle in order to determine the diastolic blood pressure of the patient.

These and other features of the end cycle analysis technique of the present invention may be better understood by referring to FIGS. 9 and 14–21. As described previously in connection with FIGS. 9 and 11, system 100 detects R-waves and K-sounds continuously during the period in which the system is operating in the "linearly deflate" state (iv). As indicated by block 320 of FIG. 9, system 100 waits for a signal produced by ECG electrodes 110 which indicates the beginning of a new cardiac cycle. As shown in FIG. 10, the RW TIMER signal is used to gate the digitized signal derived from the output of amplifier 194 so that system 100 is sensitive only to the R-wave component of the ECG of the subject (and not, for example, the S-wave or T-wave components). In the preferred embodiment, the signal RW TIMER is raised to logic level 1 when the peak of the R-wave component of the signal derived from ECG electrodes 110 occurs, and is held at logic level 1 for 300 ms, after which period it falls to logic level 0.

In the preferred embodiment, the signal K WINDOW shown in FIG. 11(c) rises 150 milliseconds after the signal RW TIMER rises, and remains asserted for 150 milliseconds. It is during the period that the signal K WINDOW is at logic level 1 that system 100 detects K-Korotkoff sounds. The delay of 150 milliseconds from the time an R-wave is detected until the time system 100 begins looking for a Korotkoff sound is provided to give the blood pressure head time to travel from the heart of the subject to the subject's arm (where cuff 114 and K-sound transducer 108 are located).

In the preferred embodiment, the R-wave window (corresponding to the time the signal RW TIMER is at logic level 1) and the K-sound window (corresponding to the time the signal K WINDOW is at logic level 1) close at the same time (about 300 ms after the peak of the R-wave occurs).

A K-sound measurement and a corresponding cuff pressure measurement are stored in RAM 132 for each cardiac cycle (i.e., for each R-wave) occurring during the linearly deflate state (iv) in the preferred embodiment. As described previously, the output of K-sound transducer 108 is amplified by K-sound amplifier 174, filtered by low pass filter 176, and converted to an absolute value by absolute value circuit 178. The output of absolute value circuit 178 is digitized by analog-to-digital converter 172, and the digitized value is made available to digital signal processor 102. ADC 172 continuously samples and digitizes the outputs of absolute value circuit 178 and amplifier 168 at a predetermined sampling rate, and makes these signals available to digital processor 102 as the digital values KSAMP and PSAMP, respectively. The digitized K-sound value KSAMP indicates the magnitude (absolute value) of the filtered, amplified output of K-sound transducer 108. Digital processor 102 stores one digitized value indicating K-sound amplitude for each cardiac cycle in a buffer area of RAM 132 set aside for this purpose, together with the processed output of pressure transducer 106 PSAMP (i.e., the digitized output of amplifier 168) indicating the pressure present in cuff 114 at the time the stored K-sound value was detected (block 323).

Figure 14A:
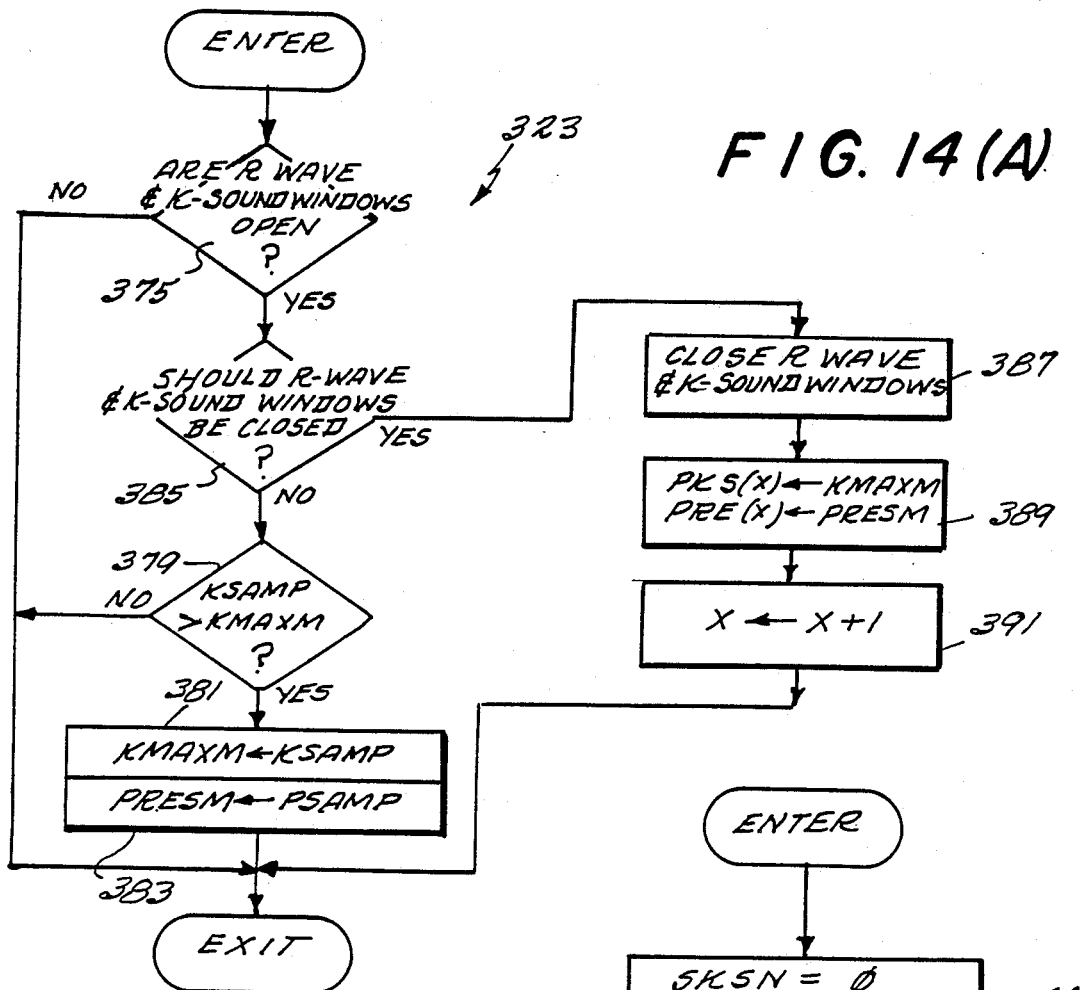
FIG. 14(A) is a detailed flow chart of the steps performed by block 323 shown in FIG. 9.
Figure 14B:
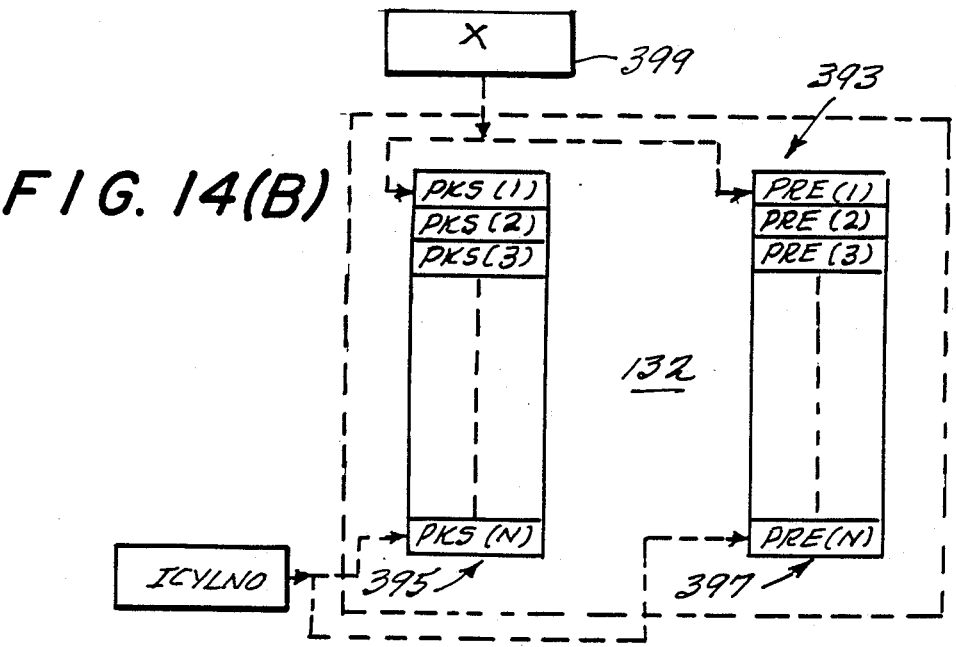
FIG. 14(B) is a schematic diagram of the register files within RAM 132 shown in FIG. 1 used to store K-sound and cuff pressure values.
Figure 14C:
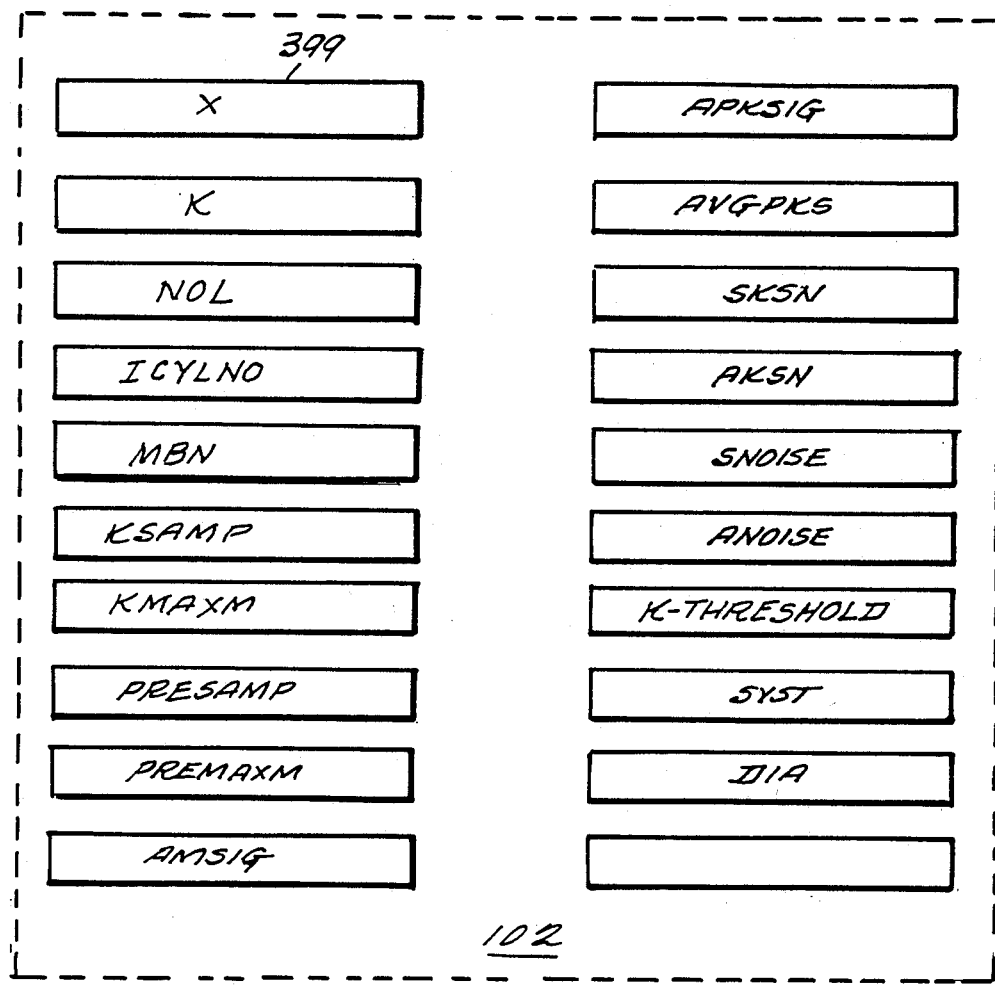
FIG. 14(C) is a schematic diagram of some of the registers and/or storage locations of digital processor 102 used to store and/or calculate values.

FIG. 14(C) is a schematic diagram of some of the storage locations used by digital processor 102 to perform the steps shown in FIGS. 14(A), and 15–19. These storage locations may be registers internal to processor 102 or storage locations of RAM 132, as will be understood by those skilled in the art. Digital processor 102 may manipulate the contents of these storage locations and registers as desired (e.g., decrement or increment the contents, add to or subtract from the contents, clear the contents, etc.). Some of the storage locations shown are double-precision in order to reduce errors in the calculations to be performed. The significance of the contents of the storage locations shown in FIG. 14(C) will be discussed in detail in connection with FIGS. 14(A) and 15–19.

FIG. 14(a) is a detailed flow chart of the steps performed by block 323 of FIG. 9. Upon detection of an R-wave (block 320), a register KMAXM of digital processor 102 is cleared—this register is used to store the maximum digitized signal output of absolute value circuit 178 during the cardiac cycle initiated by the R-wave. Decision block 375 determines whether the R-wave window is open (in the preferred embodiment, by testing to see whether the signal RW TIMER shown in FIG. 10 is at logic level 1), and whether the Korotkoff sound detection window is open (in the preferred embodiment, by testing to see whether the signal K WINDOW shown in FIG. 11(c) is at logic level 1). If either the R-wave window or the K-sound window are not open, system 100 ignores the values representing K-sound level and cuff pressure level. If, however, both the R-wave window and the K-sound window are open (decision block 375), system 100 determines whether the windows should be closed (by determining whether 300 ms has elapsed since the R-wave window was opened) (block 385). If the windows should not be closed yet, system 100 tests the K-sound signal level KSAMP to ascertain whether it exceeds the maximum level measured so far for that cardiac cycle (decision block 379). Decision block 379 compares the value KSAMP (the most recently sampled Korotkoff sound signal level produced by ADC 172) with the value KMAXM (the largest average Korotkoff sound signal level sampled so far during the present cardiac cycle) (KMAXM is cleared to zero each time a new R-wave is received). If KSAMP≦KMAXM, the present Korotkoff sound signal level KSAMP is less than a previously measured Korotkoff sound signal level for the same cardiac cycle, and is therefore ignored. If, however, KSAMP>KMAXM, the most recently sampled Korotkoff sound signal level is the highest level measured so far for the present cardiac cycle, and this value KSAMP is written into the register KMAXM to replace the value previously contained by the register (block 381). Simultaneously or immediately thereafter, the value PSAMP (the present output of ADC 172 corresponding to the most recently sampled digitized, amplified output of cuff pressure transducer 106) is written into another register PRESM as the pressure of cuff 114 at the instant the maximum K-sound level occurred (block 383).

Decision block 385 determines whether the R-wave window and the K-sound window should be closed (by determining whether predetermined periods of time have elapsed since these windows were opened, as discussed above). If the K-sound and R-wave windows should remain open (i.e. these predetermined periods of time have not yet elapsed), the "linearly deflate" state (iv) is permitted to continue and blocks 310–323 are executed once again. If, on the other hand, decision block 385 determines that the R-wave and K-sound windows should be closed (and thus, the present cardiac cycle should be considered as having ended), these windows are closed (in the preferred embodiment by causing the signal RW TIMER to drop from logic level 1 to logic level 0 and causing the signals K WINDOW to likewise drop from logic level 1 to logic level 0) (block 387).

Blocks 375–383 are thus performed repeatedly at a predetermined rate. When the R-wave window and the K-sound window opened during a cardiac cycle are both closed (blocks 385, 387), register KMAXM contains the maximum (peak) K-sound level measured during the cardiac cycle (this maximum level corresponds to the absolute value of the peak amplitude of the output of K-sound transducer 108 occurring during the cardiac cycle after unwanted frequency components have been removed by filter 176), and the register PRESM contains the pressure of cuff 114 at the instant the maximum K-sound level occurred.

A number of consecutive storage locations in RAM 132 are allocated for use as a temporary buffer 393 (shown in FIG. 14(B)). Buffer 393 stores peak Korotkoff sound levels, in digital form, for each cardiac cycle of a cuff cycle (in a register file 395) and the cuff pressure values (also in digital form) corresponding to those peak Korotkoff sound levels for each cardiac cycle of the cuff cycle (in a register file 397). Thus, the storage location PKS(1) contains the peak Korotkoff sound level for the first cardiac cycle in the present cuff cycle, and the storage location PRE(1) contains the value representing the pressure of cuff 114 at the instant this peak Korotkoff sound level was detected. Similarly, the storage location PKS(2) and PRE(2) contain, respectively, the peak Korotkoff sound level and the corresponding cuff pressure value for the second cardiac cycle of the cuff cycle, and the locations PKS(n) and PRE(n) contain the peak Korotkoff sound level and the corresponding cuff pressure value for the nth cardiac cycle of the cuff cycle. The lengths of register files 395 and 397 are sufficient to store Korotkoff sound level and corresponding cuff pressure values for 200 cardiac cycles in the preferred embodiment.

Register x (399) is used as a pointer to address the locations in register files 395 and 397. In the preferred embodiment, the x register is simply an index addressing register which, together with one or more base addressing registers (not shown), directly addresses storage locations in RAM 132. For example, when x=1, x register 399 points to storage location PKS(1) of register file 395 and storage location PRE(1) of register file 397 simultaneously. Thus, digital processor 102 can access the storage locations of register files 395 and 397 corresponding to a particular cardiac cycle (e.g. the first heartbeat, the second heartbeat, the nth heartbeat, etc.) occurring during the "linearly deflate" state (iv)) by merely writing the cardiac cycle number in the x register 399.

At the end of a cardiac cycle (decision block 385 of FIG. 14(a)), after the R-wave and K-sound windows have been closed (by block 387), digital processor 102 stores the values KMAXM and PRESM into register files 395, 397, respectively, by performing the following assignments:

PKS(x)←KMAXM

PRE(x)←PRESM, where x is the number of the cardiac cycle just ended (block 389). Block 391 then increments the contents of x register 399 in preparation for the next cardiac cycle.

As already described, blocks 310–323 shown in FIG. 9 are executed continuously until the pressure of cuff 114 falls below a cuff pressure lower limit. Depending upon the heart rate of the subject and the duration of the "linearly deflate" (iv) state, block 320 may detect a relatively large number of R-waves, block 322 may detect a relatively large number of corresponding peak Korotkoff sound levels, and block 323 may store this relatively large number of corresponding Korotkoff sound levels and associated cuff pressure values in buffer 393. When the pressure of cuff 114 finally falls below the cuff pressure lower limit (i.e., when the result of the decision performed by decision block 318 of FIG. 9 is "yes"), buffer 393 contains the peak Korotkoff sound level and corresponding cuff pressure value for each and every cardiac cycle (i.e., heartbeat) occurring during the "linearly deflate" state (iv).

Figure 15:
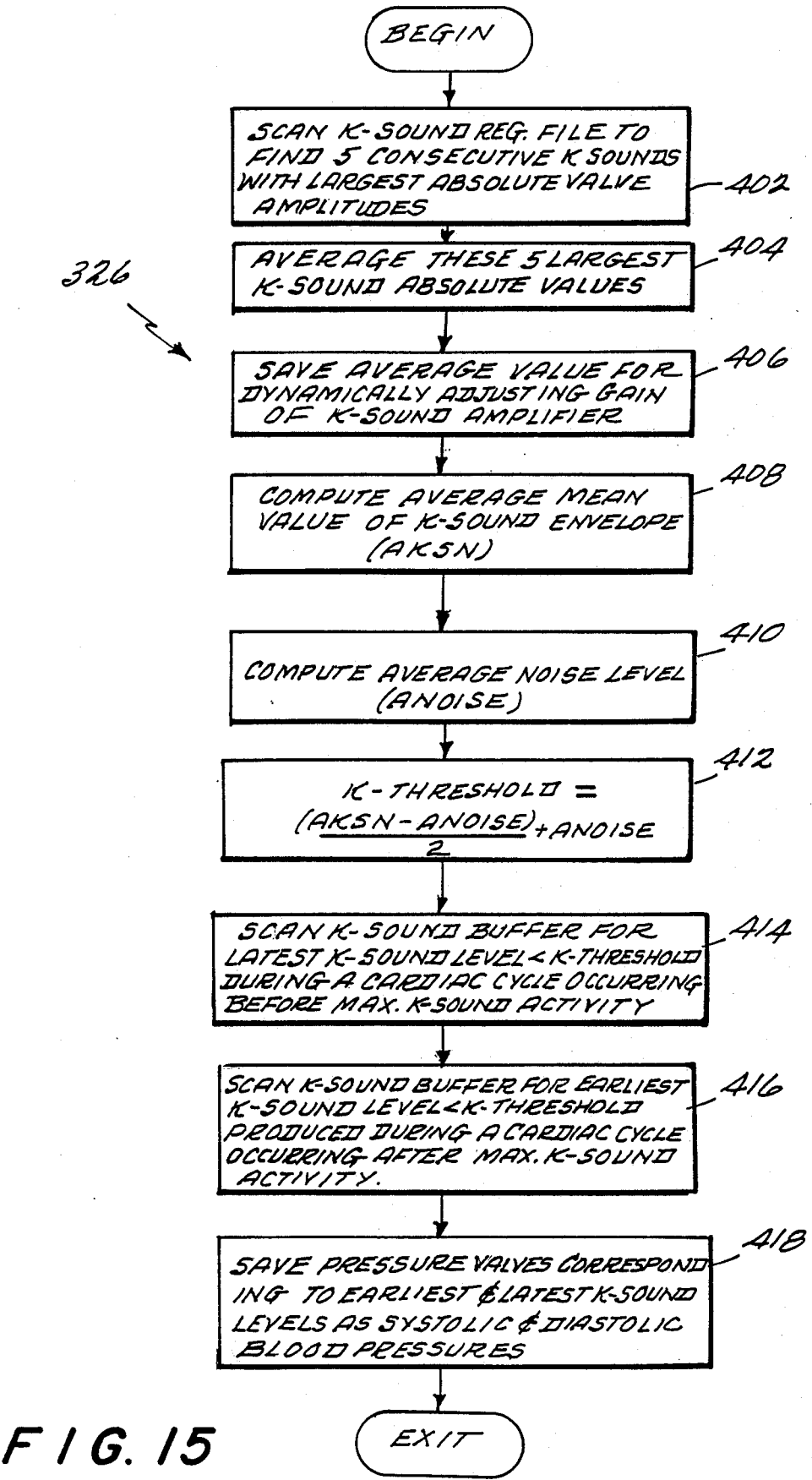
FIG. 15 is a flow chart of the steps performed by block 326 shown in FIG. 9.

System 100 in the preferred embodiment analyzes this complete history of peak Korotkoff sound level and corresponding cuff pressure for each cardiac cycle occurring during cuff deflation *after* the system enters the "rapid deflate" state (v), in blocks 326 and 327. FIG. 15 is a flow chart of the steps performed by block 326 shown in FIG. 9.

It has been found through study of the K-sound envelope of many patients that the Korotkoff sound activity produced during cuff deflation exhibits a single maximum. During this period of maximum activity, which lasts for four to five cardiac cycles for most subjects, the magnitude (i.e. loudness) of Korotkoff sounds produced by the subject is substantially greater than the magnitude (i.e. loudness) of Korotkoff sounds occurring before and after the period. Sometimes a phenomenon known as "upstream pounding" generates sounds of relatively high amplitude that appear to be but are not Korotkoff sounds soon after cuff deflation begins—but the amplitudes of these sounds are generally not as high as those of the amplitudes of the Korotkoff sounds during maximum Korotkoff sound activity, and usually such sounds are produced for less than 4cardiac cycles. System 100 scans register file 395 to find the five consecutive peak Korotkoff sound levels with the largest absolute value amplitudes (block 402). The average of these 5 levels is computed (block 404) and stored for use in determining whether the gain of K-sound amplifier 174 should be dynamically adjusted (block 406).

Next, the average mean value of all of the K-sound levels measured for the entire cuff cycle is computed (block 408). As will be understood, only noise and/or artifacts will be detected during some cardiac cycles (e.g., when the pressure of cuff 114 exceeds the systolic blood pressure of the subject or is less than the diastolic blood pressure of the subject, or when a so-called "auscultatory gap" occurs). The signal level at the output of absolute value circuit 178 during other cardiac cycle may include components resulting from a weak Korotkoff sound, together with ambient noise and/or artifact components. Block 408 averages the peak Korotkoff sound levels measured for all of the cardiac cycles of the cuff cycle to produce a mean value AKSN.

An average noise level (ANOISE) is then computed by averaging all of the measured K-sound levels which fall below the average mean value of the K-sound envelope AKSN computed by block 408 (block 410). A threshold value K-THRESHOLD is computed by averaging AKSN and ANOISE and adding to this average the value ANOISE (block 412). K-THRESHOLD is used to find the K-sound levels corresponding to the K-sounds occurring during systole and diastole so that the systolic and diastolic blood pressures of the subject can be ascertained.

Register file 395 is scanned in two directions, beginning at the K-sound level determined by block 402 to be the center of K-sound activity (block 414). Locations of register file 395 storing peak K-sound levels measured during cardiac cycles occurring before the center of K-sound activity are compared with the dynamic threshold level K-THRESHOLD computed by block 412 to locate the cardiac cycle occurring latest in time but prior to maximum K-sound activity which produced a K-sound level less than K-THRESHOLD (block 414). Similarly, locations of register file 395 corresponding to cardiac cycles occurring after the cardiac cycle at the center of maximum K-sound activity to locate the cardiac cycle occurring earliest in time but after the maximum K-sound activity which produced a K-sound level which is below K-THRESHOLD (block 416). The pressure of cuff 114 measured during the latest cardiac cycle occurring prior to the period of maximum K-sound activity which produced a K-sound having a level less than K-THRESHOLD is taken as the systolic blood pressure of the subject. The pressure of cuff 114 measured during the earliest cardiac cycle occurring after the period of maximum K-sound activity producing a K-sound having a level less than K-THRESHOLD is taken as the diastolic blood pressure of the patient.

The pressure values resulting from blocks 414 and 416 are saved as the systolic and diastolic blood pressures of the subject for the cuff cycle being analyzed (block 418), and are stored in RAM 132 (in a permanent register file not shown) along with heart rate, time and sample number (block 327 of FIG. 9). These values are also displayed on display 140 (block 328).

Figure 16:
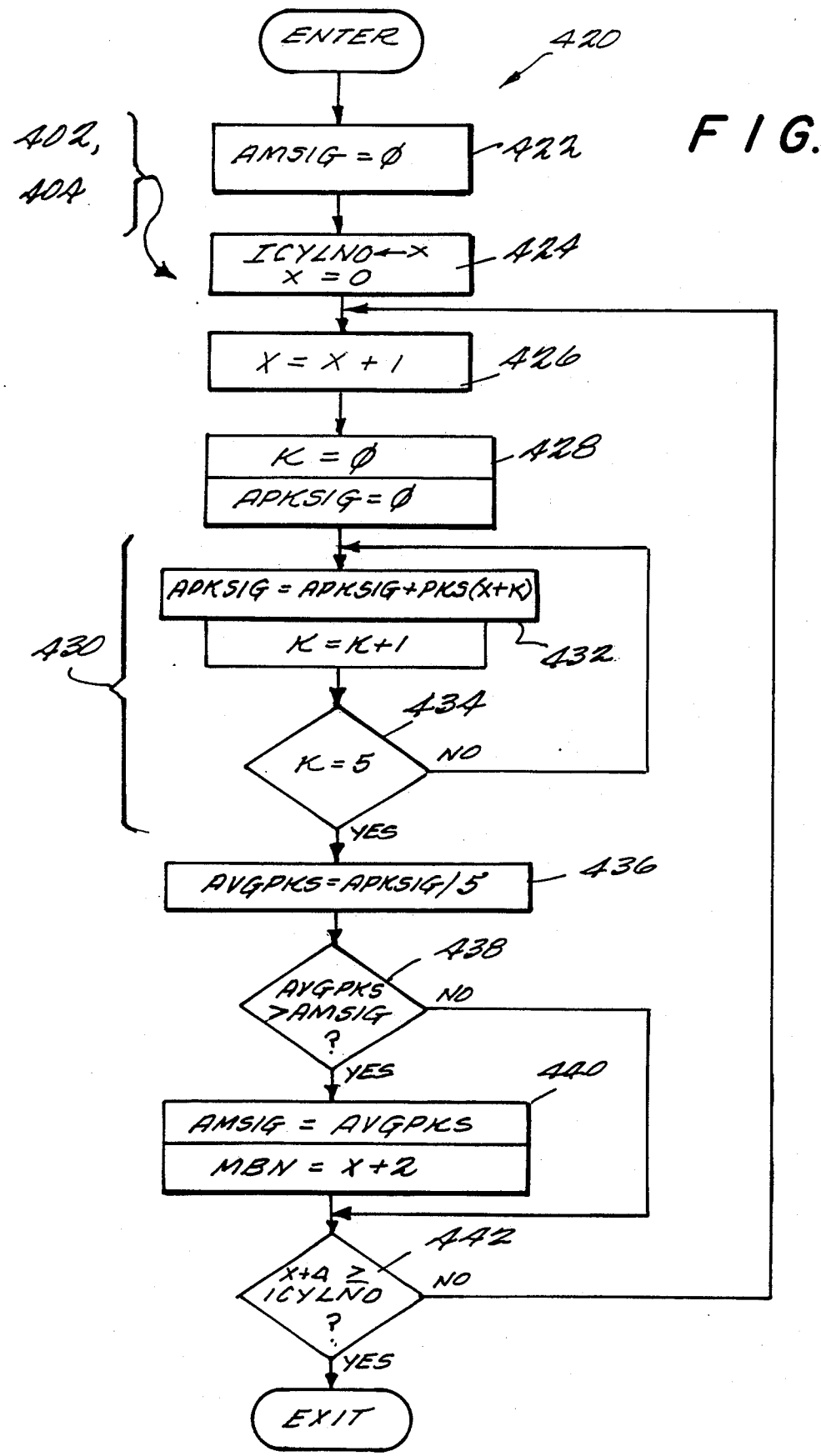
FIG. 16 is a detailed flow chart of the steps performed by blocks 402 and 404 shown in FIG. 15.

FIG. 16 is a detailed flow chart of blocks 402 and 404 shown in FIG. 15. Although blocks 402 and 404 are shown in FIG. 15 as separate, consecutively performed steps, the average of the five largest K-sound absolute values determined by block 404 is used by block 402 to determine that the five largest K-sound absolute values have been located. Thus, blocks 402 and 404 are performed together in one integrated routine 420 in the preferred embodiment. The function of routine 420 is to compute the average of every five consecutive peak K-sound levels stored in register file 395 to determine which five consecutive levels have the highest average level—and by using this technique, determine the cardiac cycle at the center of the maximum Korotkoff sound activity occurring during the cuff cycle.

A register AMSIG (average maximum signal) is used as a temporary storage location, and at any given time contains the maximum average K-sound level found so far for five consecutive K-sounds. AMSIG is initially cleared (block 422). The x register contains the number of cardiac cycles which occurred during the linearly deflate state (iv). This number is saved in a storage location ICYLNO, and the x register is then cleared (block 424). The contents of x register 399 is incremented (block 426), and the contents of a loop counter k and a summing register APKSIG are cleared (block 428). A loop 430 is then performed five times to sum the peak K-sound levels for cardiac cycles x, x+1, x+2, x+3 and x+4 in the register APKSIG. When loop counter k is equal to 5 (decision block 434), a 5 K-sound average peak value AVGPKS is computed by dividing the APKSIG sum (computed by block 432) by five to obtain the average peak Korotkoff sound level for cardiac cycles x through x+4 (block 436). If the value AVGPKS≦AMSIG, then AVGPKS is less than an average peak Korotkoff sound level of five earlier-occurring cardiac cycles (decision block 438), and control is transferred to decision block 442. If, however, AVGPKS>AMSIG, the value AVGPKS corresponds to the highest average peak K-sound level found so far for five consecutive cardiac cycles, and the contents of register AMSIG is replaced by AVGPKS (block 440). Into another register MBN (mean beat number) is stored the value x+2 (block 440). Register MBN thus contains the number of the center one of the five cardiac cycles found by decision block 438 to have the highest average peak K-sound level.

The steps of blocks 426-442 are continuously performed until decision block 442 determines that all consecutive groups of the five cardiac cycles have been tested (i.e., the x+4th, that is, the 5th cardiac cycle of the group of 5 cardiac cycles being examined is equal to the number of cardiac cycles ICYLNO). Thus, the loop formed by blocks 426-442 tests first cardiac cycles 1-5, then cardiac cycles 2-6, then cardiac cycles 3-7, . . . , and finally cardiac cycles n-4 through n (where n is the last cardiac cycle). When the entire contents of register file 395 have been processed by routine 420, register MBN contains the cardiac cycle at the center of the maximum K-sound activity, and register AMSIG contains the average peak K-sound level of the group of five consecutive cardiac cycles centered about cardiac cycle MBN.

Figure 17:
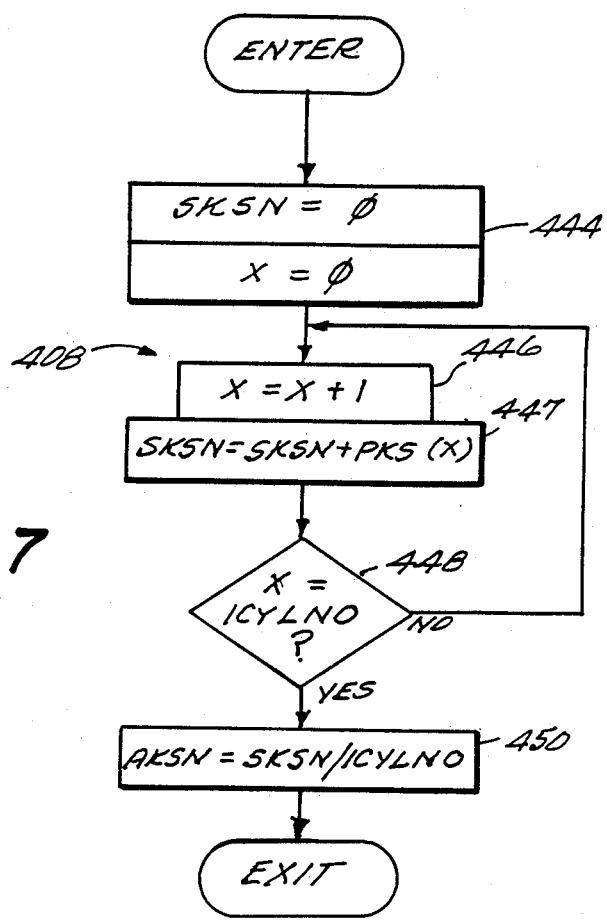
FIG. 17 is a detailed flow chart of the steps performed by block 408 shown in FIG. 15.

FIG. 17 is a detailed flow chart of block 408 shown in FIG. 15. Block 408 computes the average mean amplitude of the entire K-sound envelope and stores this mean value in a register AKSN. A summing register SKSN is cleared, as is x register 399 (block 444). Every peak K-sound level contained in register file 395 is summed into register SKSN. The loop formed by blocks 446 and 448 simply advances through register file 395, reads the values PKS(1) through PKS(n), one at a time, and adds the read values to the contents of register SKSN. When the last entry PKS(n) of register file 395 has been read and summed into register SKSN (as tested for by decision block 448), summing register SKSN contains the sum of all of the values stored in register file 395. The average value AKSN of the peak K-sound levels stored in register file 395 is obtained by dividing the sum SKSN by the number of cardiac cycles ICYLNO (block 450). The value AKSN is the average mean peak K-sound level for every cardiac cycle of the cuff cycle for which a measurement was performed.

Some of the values averaged to produce AKSN do not correspond to actual K-sound levels, since the preferred embodiment stores a value in register file 395 for each and every cardiac cycle occurring during the "linearly deflat" state (iv) whether or not the value actually corresponds to a K-sound (thus, some values represent only noise and/or artifacts present before cuff pressure fell below the subject's systolic blood pressure or after the cuff pressure fell below the patient's diastolic blood pressure). These values are nevertheless averaged in order to weight the value of AKSN slightly on the low side if a clear, textbook K-sound envelope was present with little noise and artifact components.

Figure 18:
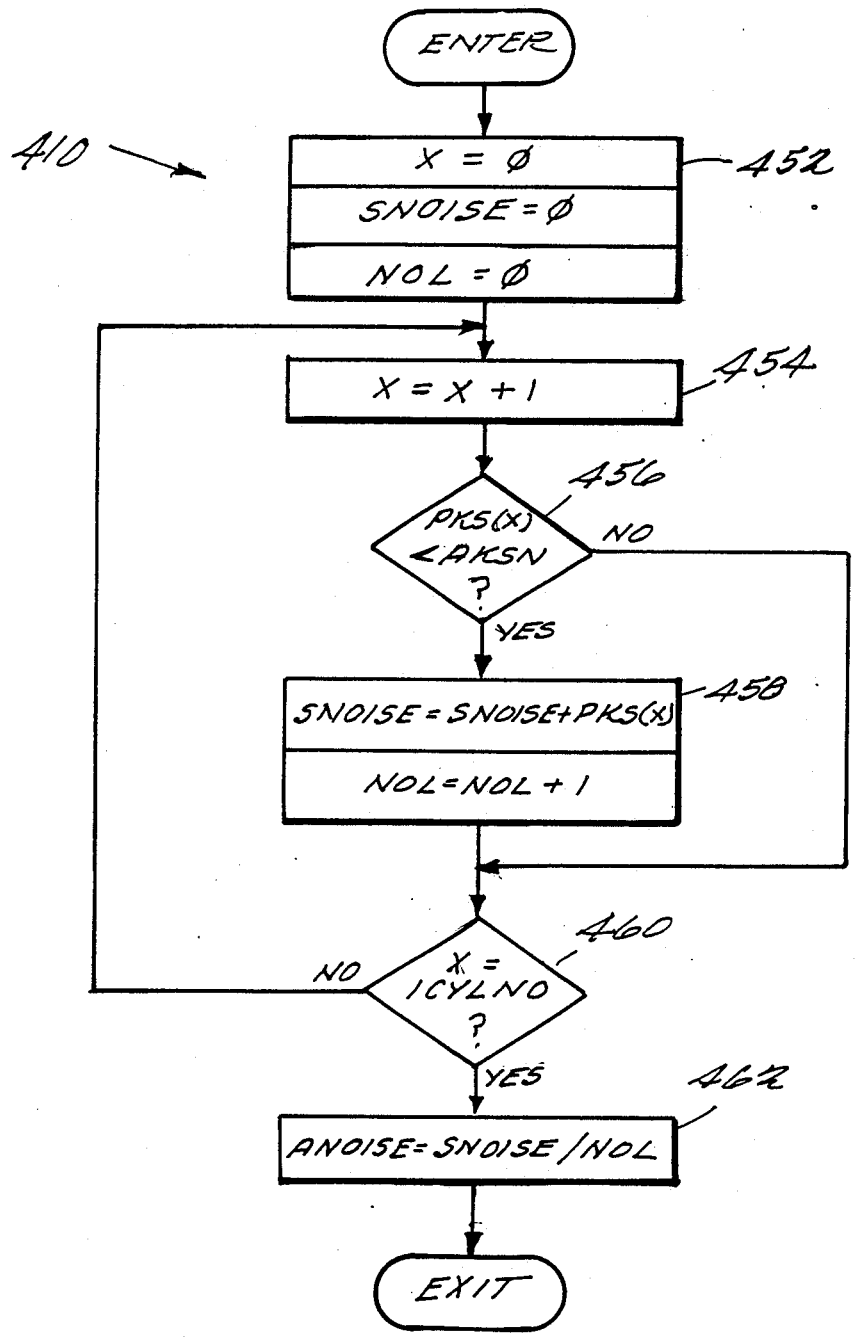
FIG. 18 is a detailed flow chart of the steps performed by block 410 shown in FIG. 15.

FIG. 18 is a detailed flow chart of the steps performed by the "compute average noise level" block 410 shown in FIG. 15. Block 410 computes the average noise level ANOISE received during the last cuff cycle by assuming all of the measured peak Korotkoff sound levels not exceeding the mean K-sound level AKSN computed by block 408 are attributable to noise and/or artifact, and averaging all such levels. Initially, x register 399 is cleared, as is a summing register SNOISE and a counter register NOL (block 452). The contents of x register 399 is incremented (block 454), and decision block 456 reads, from register file 395, the peak Korotkoff sound level measured during the cardiac cycle corresponding to the value contained in the x register and compares that peak Korotkoff sound level with the average mean K-sound level value AKSN computed by block 408. If PKS(x)≧AKSN, system 100 assumes the level represents a Korotkoff sound and not merely noise. If, on the other hand, PKS(x)<AKSN, system 100 determines this peak Korotkoff sound level is attributable to mostly noise and/or artifact, and adds the level to the contents of the summing register SNOISE (block 458). Block 458 also increases the count of counter NOL. The contents of x register 399 is then compared with the number of cardiac cycles measured during the last cuff cycle (ICYLNO) to determine if the last peak Korotkoff sound level PKS(n) has been read and tested by decision block 456 (block 460). If some measured peak Korotkoff sound levels have not yet been tested, control returns to block 454 so that these remaining values can be read and tested. Otherwise, the average noise level ANOISE is calculated by dividing the contents of summing register SNOISE (which contains the sum of all of the peak Korotkoff sound levels not exceeding the mean peak Korotkoff sound level AKSN) by the number of such values NOL which were summed (block 462). The resulting average noise level value ANOISE is used as a lower limit for the value K-THRESHOLD computed by block 412.

Block 408 thus computes the average mean value of the K-sound levels (AKSN) measured for all cardiac cycles occurring during the cuff cycle. Block 410 computes the average noise level ANOISE of the entire K-sound envelope by averaging all of the measured peak Korotkoff sound levels which do not exceed the average mean peak Korotkoff sound level computed by block 408. Block 412 computes a threshold value K-THRESHOLD according to the following equation:

$$K\text{-THRESHOLD} = \frac{(AKSN - ANOISE)}{2} + ANOISE.$$

K-THRESHOLD as calculated lies halfway between the average K-sound envelope level AKSN and the average noise level ANOISE, and under normal operating conditions of system 50, is generally approximately 25% of the K-sound envelope amplitude.

Because the value K-THRESHOLD is computed from the average noise level and the average K-sound level of the measurements for the cuff cycle to be analyzed, it is normalized not only or the particular subject wearing cuff 114, but also for the particular cuff cycle being analyzed. The Korotkoff sound envelope obtained from a subject may change from one cuff cycle to the next or even during a single cuff cycle for a variety of reasons. The Korotkoff sound envelope produced by some subjects changes with time during a cuff cycle for physiological reasons which are not fully understood. Sometimes, a particular activity in which the subject is engaged (e.g., running up a flight of stairs, driving an automobile, walking briskly, etc.) causes physiological changes and/or changes in the position of the arm on which cuff 114 is strapped which can change the noise and artifact level as well as the mean peak Korotkoff sound level obtained for a cuff cycle. By computing K-THRESHOLD from data obtained for the cuff cycle under analysis, it is possible to generate far more accurate results which are normalized for that cuff cycle.

Figure 19:
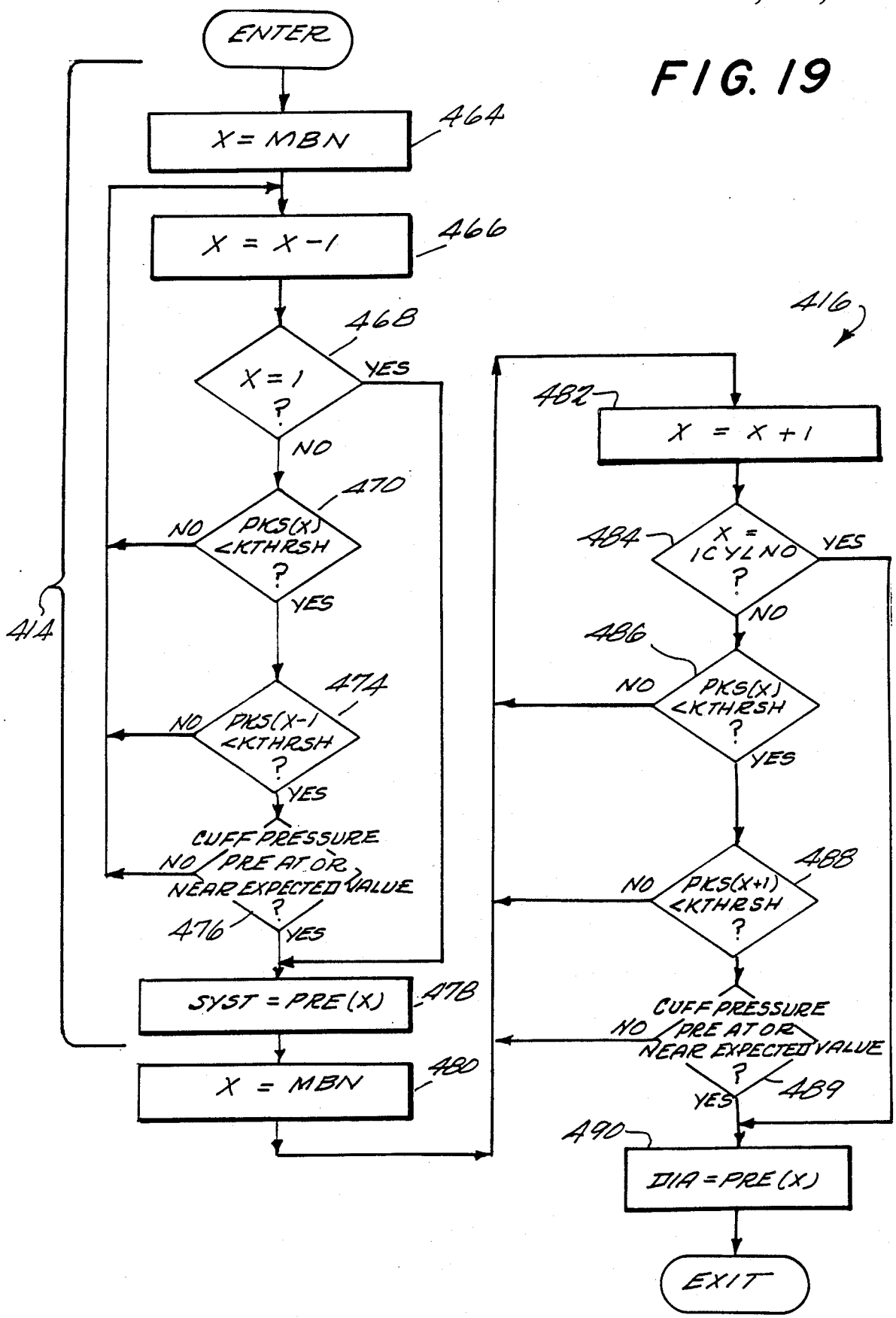
FIG. 19 is a detailed flow chart of the steps performed by blocks 414 and 416 shown in FIG. 15.

FIG. 19 is a detailed flow chart of the steps performed by blocks 414 and 416 shown in FIG. 15. Block 414 uses the value K-THRESHOLD computed by block 412 to locate the latest K-sound level occurring before the peak K-sound activity which does not exceed K-THRESHOLD—the stored pressure value of cuff 114 corresponding to this peak K-sound level was measured is taken as the systolic blood pressure of the subject. Block 416 determines the peak K-sound measured earliest in time after the maximum Korotkoff sound activity occurred which does not exceed the value K-THRESHOLD—the corresponding stored pressure of cuff 114 is taken as the diastolic blood pressure of the patient.

The value MBN (maximum beat number) computed by block 402 is stored in x register 399, so that the x register points to the location in register file 395 storing the peak Korotkoff sound level for the cardiac cycle at the center of maximum Korotkoff sound activity (block 464). The contents of x register 399 is decremented (block 466) and tested to determine whether it is equal to 1 (to see whether it points to the location of register file 395 storing the peak Korotkoff sound level for the first cardiac cycle) (decision block 468). If x>1, the peak Korotkoff sound level to which the x register points PKS(x) is compared with the value K-THRESHOLD computed by block 412 (decision block 470). If PKS(x)≧K-THRESHOLD, cardiac cycle x is not considered to be the cardiac cycle during which the subject's systolic blood pressure was measured, and control is returned to block 466 so that the Korotkoff sound level from a still-earlier cardiac cycle may be examined.

If PKS(x)<K-THRESHOLD, then cardiac cycle x is tentatively determined to be the cardiac cycle corresponding to systolic pressure. However, occasionally no or only weak K-sounds are produced during cardiac cycles not corresponding to systolic pressure, and the K-sound levels measured for cardiac cycles both before and after these one or two cardiac cycles may thus lie above K-THRESHOLD. System 100 insures that the cardiac cycle tentatively determined by decision block 470 to correspond to systole is not merely a "drop-out" or an "auscultatory gap" by determining whether the peak K-sound level of the previous adjacent cardiac cycle is also below K-THRESHOLD (decision block 474) and cuff pressure is on "linear track" (block 476).

Occasionally, an "auscultatory gap" (i.e., one or more "missed" K-sounds) can occur which can potentially introduce error into the selection of stored cuff pressure values corresponding to the subject's systolic and/or diastolic blood pressure. Suppose, for example, that just as (or soon after) the pressure within cuff 114 falls to a pressure equal to the systolic blood pressure of the subject, sufficient pressure is exerted upon an external wall of cuff 114 (e.g., by flexing of the subject's biceps, by the subject resting his arm on a tabletop, etc.) to temporarily increase the pressure within the cuff to greater than the subject's systolic blood pressure. System 100 might detect several K-sound levels of relatively high amplitude representing K-sounds resulting from normal linear cuff deflation, and then, when the pressure within cuff 114 rises abnormally to occlude the brachial artery once again, detect much lower "K-sound" levels (i.e., detect an "auscultatory gap"). This gap in the measured peak K-sound levels attributable to actual K-sounds might be mistaken by block 486 for the latest peak K-sound level below K-THRESHOLD.

In the preferred embodiment, two "tests" are performed to reduce the possibility that incorrect cuff pressure values are selected as corresponding to the subject's systolic/diastolic blood pressures because of an "auscultatory gap". Block 474 ensures that short-lived gaps are not mistaken for systole by confirming the peak K-sound level measured from the previous one or two cardiac cycles (i.e., cardiac cycles x-1 and x-2) are also below K-THRESHOLD. In order to prevent longer-term auscultatory gaps caused by abnormally high cuff pressure from being mistaken for systole, block 476 verifies that the pressure of cuff 114 PRE measured for cardiac cycle x is at an expected value (within an error tolerance dependent upon rate of deflation). The expected pressure is determined from the software model discussed earlier as a function of cardiac cycle (time). If block 476 determines the stored pressure PRE is outside of a range of error centered at the expected pressure value, (i.e. the cuff pressure is not on "linear track"), an auscultatory gap is considered to have occurred during cardiac cycle x and still earlier cardiac cycles are examined (block 466).

Thus, if the stored pressure PRE is at or near the expected value and if PKS(x-1)<K-THRESHOLD and PKS(x)<K-THRESHOLD, then system 100 determines x to correspond to systole, reads the cuff pressure value PRE(x) corresponding to this cardiac cycle from register file 397, and stores this read cuff pressure value in a holding register SYST (block 478). If PKS(x-1)≧K-THRESHOLD, on the other hand, system 100 decides the cardiac cycle x isolated by decision block 470 does not correspond to systole, and control is returned to block 466 so that still earlier cardiac cycles can be tested. Decision block 474 preferably also tests whether PKS(x-2)<K-THRESHOLD, thus insuring that at least the two cardiac cycles immediately preceding cardiac cycle x both produced peak K-sound levels which were below K-THRESHOLD (it is very rare that an auscultatory gap or a drop-out will last for more than two cardiac cycles).

If decision block 468 determines that x=1, then the cuff pressure corresponding to the first cardiac cycle measured, PRE(1), is taken to be the systolic blood pressure of the subject. This first cardiac cycle never, however, corresponds to systole if other parameters of system 100 (e.g. inflation pressure of cuff 114) have been set correctly, and is thus merely a default value. When block 478 is finally performed, the systolic blood pressure SYST is taken to be the cuff pressure measured during the last cardiac cycle in time occurring *prior* to maximum K-sound activity which produced a peak K-sound level less than K-THRESHOLD.

This systolic blood pressure value does not necessarily and typically does not correspond to the pressure within the cuff 114 when first K-sound occurring during the cuff cycle was detected. As will be discussed in connection with FIGS. 20 and 21, the technique of determining systole in accordance with the present invention is far more accurate and error-free than the prior-art method of attempting to detect, in real time, the first K-sound which occurs.

Blocks 480-490 perform the steps of block 416 shown in FIG. 15. The steps performed by blocks 480-490 are very similar to the steps performed by blocks 464-478, except that blocks 480-490 scan register file 395 for values corresponding to cardiac cycles which occur after the center of K-sound activity. The value MBN is stored in x register 399 (block 480), and is then incremented (block 482) until either the end of register file 395 is reached (tested for by block 484), or until a value stored in the register file is found to be less than K-threshold (block 486). Decision block 486 tentatively determines the earliest cardiac cycle occurring after the center of K-sound activity which produced a peak Korotkoff sound level less than K-THRESHOLD to correspond to diastole, but confirms that the low peak K-sound level was not due an auscultatory gap or a drop-out by confirming that the one or two consecutive cardiac cycles thereafter also produced peak K-sound levels less than K-THRESHOLD (decision block 488) and cuff pressure was on linear track (decision block 489). If PKS(x)<K-THRESHOLD and PKS(x+1)<K-THRESHOLD (and, in the preferred embodiment PKS(x+2)<K-THRESHOLD), cardiac cycle x is assumed to correspond to diastole, the cuff pressure value stored for cardiac cycle x (PRE(x)) is obtained from register file 397 and stored in a holding register DIA (block 490). Otherwise, later cardiac cycles are tested by blocks 482-488 to see if the conditions are met for those later cycles.

After block 416 has been performed, the holding register SYST contains the systolic blood pressure of the subject, and the holding register DIA contains the subject's diastolic blood pressure. These values are stored in a protected area of RAM 132 in digital form (along with heart rate, time of day and sample number) and can be later down-loaded into an external peripheral device for storage, analysis or printing, via output connector 160 as described previously (block 418). These values are also displayed on liquid crystal display 140 by block 328 shown in FIG. 9. Also at this time, the gain of K-sound amplifier 174 can be adjusted by processor 102 in response to the value AMSIG saved by block 406.

Figure 20:
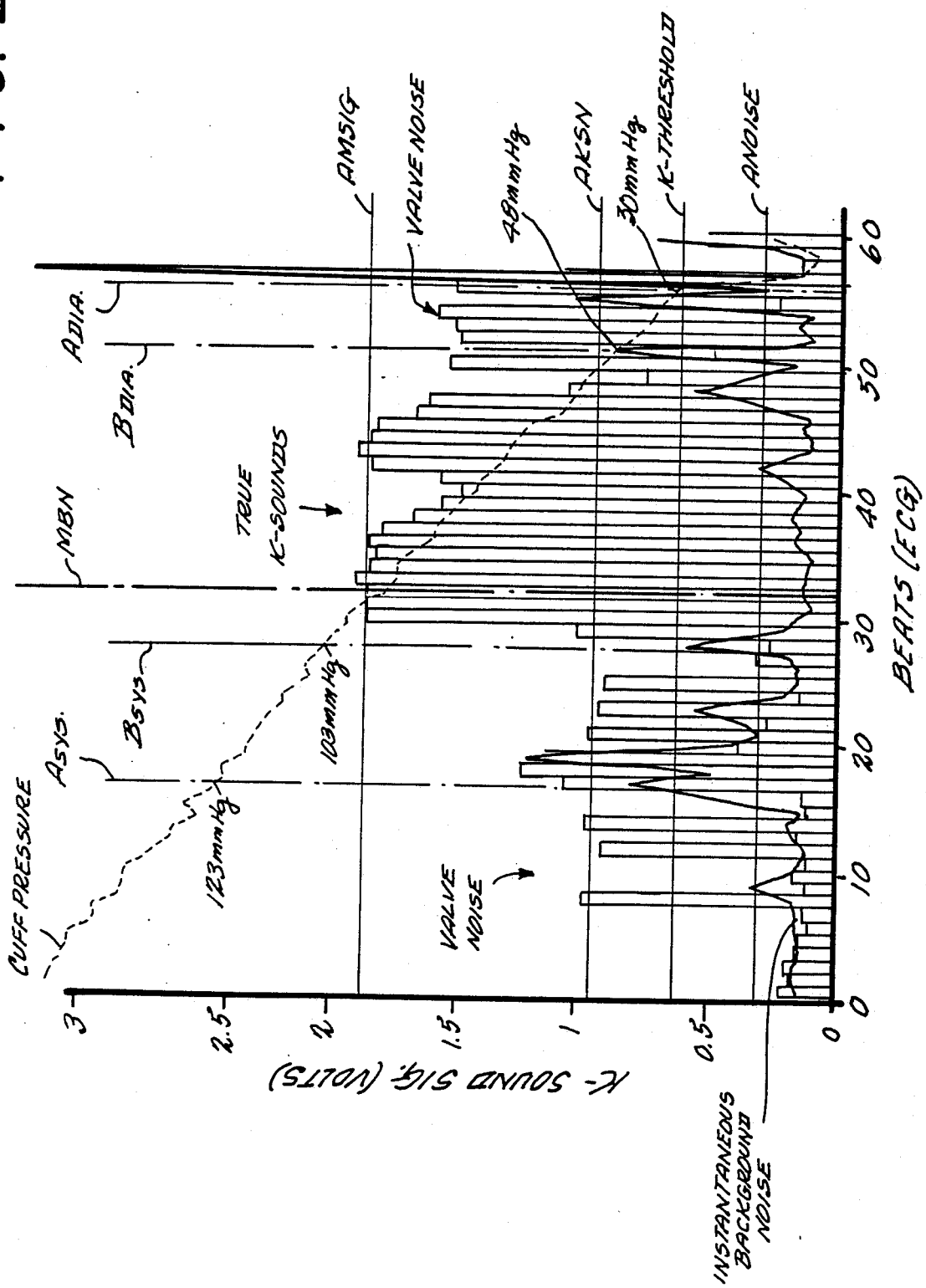
FIGS. 20 and 21 are graphical illustrations of the results of two exemplary cuff cycles produced by system 100 shown in FIG. 1.
Figure 21:
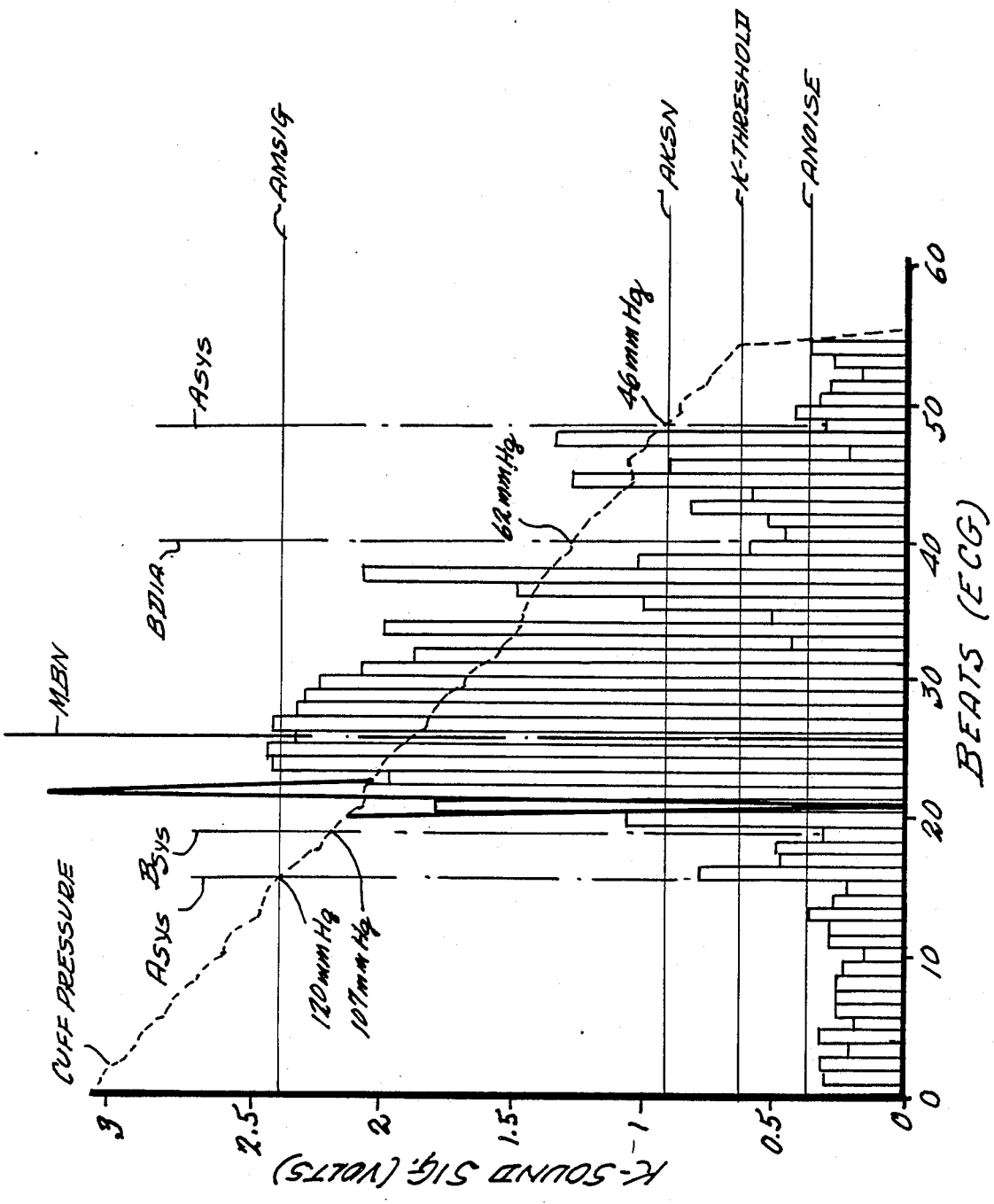

FIGS. 20 and 21 are plots of data obtained from two different, actual cuff cycle measurements performed by a prototype of system 100 on an actual subject. The abscissa of each of these plots corresponds to cardiac cycles (and thus indirectly to time) while the ordinate axis of each plot corresponds to measured K-sound signal level (in volts). The adjacent vertical bars shown are measured peak K-sound levels for each cardiac cycle (it will be recalled that the preferred embodiment measures only the peak K-sound level for each cardiac cycle, so that only one sound amplitude level for each cycle is obtained and stored). The dotted line descending from the upper left-hand corner to the lower righthand corner of each plot is the actual pressure of cuff 114.

FIG. 20 also includes a plot of instantaneous background noise with respect to cardiac cycle number (the jagged solid line at the bottom of the plot). The measurement plotted in FIG. 20 was not "clean" at all, since valve noise (i.e., noise produced by the opening and closing of air valve 120) produced many peak "Korotkoff sound" levels at the beginning and at the end of the linearly deflate state which system 100 recorded as corresponding to Korotkoff sounds. Only the area marked "true K-sounds" in FIG. 20 represents peak K-sound levels produced by actual Kootkoff sounds.

FIGS. 20 and 21 both show the parameters MBN, AMSIG, AKSN, K-THRESHOLD and ANOISE discussed in connection with FIGS. 14-19. For the measurement shown in FIG. 20, the center of Korotkoff sound activity was determined to be cardiac cycle number 32 (i.e. MBN=32), and the average mean peak K-sound level corresponding to the five cardiac cycles centered around cardiac cycle 32 (i.e. cardiac cycles 30-35) was found to be approximately 1.9 volts (see the horizontal line labelled AMSIG). The average mean value of the K-sound envelope AKSN (computed by block 408) was found to be slightly under 1.0 volts, and the average noise level ANOISE was found to be about 0.3 volts. The value K-THRESHOLD was calculated by block 412 to be approximately 0.65 volts. Block 414 isolated cardiac cycle number 28 as corresponding to systole (a dotted vertical line $B_{sys}$ shown in the plot reflects this), and block 416 determined cardiac cycle number 51 corresponded to diastole (as indicated by the dotted vertical line shown in the plot labelled $B_{dia}$). System 100 determined the systolic and diastolic blood pressures of the subject to be 103 mmHg and 48 mmHg, respectively. These values are believed to be extremely close to the actual systolic and diastolic blood pressures of the subject (as might be obtained through invasive measurement).

FIG. 20 contains two additional dotted vertical lines, $A_{sys}$ and $A_{dia}$, which mark the cardiac cycles determined by a real time analysis algorithm (operating on the same data) as corresponding to systole and diastole. Because of the relatively large amount of valve noise occurring during measurement, the prior art real-time analysis algorithm was "confused" into selecting peak "K-sound" levels attributable to valve noise as the K-sound levels corresponding to systole and diastole. Thus, the real-time algorithm determined the systolic blood pressure of the patient to be 123 mmH$_g$ (nearly 20% higher than the actual value), and determined the diastolic blood pressure of the patient to be 30 mmH$_g$ (far lower than the actual diastolic blood pressure). The plot shown in FIG. 20 clearly demonstrates that by using the end cycle analysis technique in accordance with the present invention, systolic and diastolic blood pressure can be determined even though a substantial amount of noise containing frequency components which are the same as those contained by real K-sounds was present during the measurement.

FIG. 21 is a plot of the results of another measurement cycle performed by a prototype of system 100 in accordance with the present invention. System 100 determined the systolic and diastolic blood pressures of the subject during this measurement to be 107 and 62, respectively (see lines $B_{sys}$ and $B_{dia}$ in the FIGURE). A real-time K-sound analysis routine operating on the same data mistook noise for the K-sounds produced by systole and diastole, and erroneously determined the subject's blood pressure to be 120/46. The subject's blood pressure was manually determined, using an occluding cuff, a mercury manometer and a stethoscope, to be 109/60. It can be seen that the end cycle analysis technique in accordance with the present invention is remarkably accurate (having a correlation of between 0.95 and 0.98 with actual systolic and diastolic blood pressure), and is far superior to prior-art real-time analysis techniques.

Although only one exemplary embodiment has been described in detail above, those skilled in the art will appreciate that many variations and modifications may be made to the exemplary embodiment without departing from the novel and advantageous features of the present invention. Moreover, the present invention is by no means limited to the particular components described above, but rather, could be implemented in a variety of other ways using digital logic devices, analog signal processing devices, discrete transistor devices, etc. Accordingly, all such variations and modifications are intended to be included within the scope of the appended claims.

What is claimed is:

1. A method for automatically measuring at least one cardiovascular parameter of a subject, comprising the steps of:
   (1) producing a random value;
   (2) converting the random value produced in said producing step to a time duration;
   (3) timing said time duration;
   (4) when said time duration timed by said timing step (3) has elapsed, measuring and storing at least one cardiovascular parameter of the subject; and
   (5) repeating said producing step (1), converting step (2), timing step (3), and measuring and storing step (4) to obtain a series of measurements of said at least one parameter.

2. A method as in claim 1 wherein: said method further includes the steps, performed after said producing step (1) and before said converting step (2), of:
   determining whether the random value produced by said producing step (1) falls within a predetermined range, and
   repeating said producing step (1) and said determining step if the random value is not within said predetermined range; and
   said converting step (2) converts into time durations only random values determined by said determining step to fall within said predetermined 3. A method as in claim 2 further including the preliminary step of programming said predetermined range.

4. A method as in claim 1 wherein said measuring and storing step (4) includes the steps of:
   inflating an occluding cuff worn by said subject to a pressure in excess of the systolic blood pressure of said subject;
   continuously sensing the pressure of said cuff:
   controllably deflating said cuff;
   sensing Korotkoff sounds produced by said subject during said deflating step;
   storing indicia of said sensed sounds and pressure in analog form on an analog serial storage device;
   producing digital signals representing said cardiovascular at least one parameter of said subject in response to said pressure sensed by said cuff pressure sensing step and said sounds sensed by said Korotkoff sounds sensing step; and storing said digital signals representing said cardiovascular at least one parameter in digital form in a solid state memory device.

5. A method of automatically measuring the blood pressure of a subject comprising the steps of:
(1) inflating an occluding cuff disposed on said subject to a first predetermined pressure;
(2) deflating said cuff at a controlled rate until the pressure within said cuff falls to a second predetermined pressure less than said first pressure;
(3) during said deflating step (2), sensing the pressure within said cuff;
(4) during said deflating step (2), sensing the amplitude level of sounds generated by said subject as a result of said cuff deflation;
(5) during said deflating step (2), periodically storing levels representing said sensed pressures and sensed sound amplitude levels; and
(6) after said deflating step (2), selecting, in response to said stored sensed sound amplitude levels, the stored pressure levels indicating the systolic and diastolic blood pressures of said subject, said selecting step including the steps of:
(a) determining the time of occurrence of a predetermined number of stored sound amplitude levels measured consecutively in time which have the highest mean level, said time of occurrence being the time of the center of maximum Korotkoff sound activity;
(b) determining the stored sound amplitude level measured latest in time before said time of the center of maximum Korotkoff sound activity which is less than a predetermined threshold level;
(c) selecting as the systolic blood pressure of said subject the stored pressure level measured simultaneously with said stored sound amplitude level determined by said determining step (b);
(d) determining the stored sound amplitude level measured earliest in time after said time of the center of maximum Korotkoff sound activity which is less than said predetermined threshold level; and
(e) selecting as the diastolic blood pressure of the subject the stored pressure level measured simultaneously with said stored sound amplitude level determined by said determining step (d).

6. A method as in claim 5 wherein:
said sensing step (4) includes the steps of:
(a) sensing R-waves produced by the brain of said subject,
(b) continuously measuring the amplitude level of sound produced by said subject, and
(c) determining the sensed peak sound amplitude level occurring between each pair of adjacent R-waves sensed by said sensing step (a); and
said storing step (5) includes the step of storing each of said sensed peak amplitude levels determined by determining step (c) together with the pressure sensed by sensing step (3) occurring simultaneously with said each sensed peak amplitude levels.

7. A method as in claim 5 wherein:
said sensing step (4) includes the steps of:
detecting sounds generated by said subject as a result of deflation of said cuff, and
amplifying the sound detected by said detecting step by a predetermined gain to produce a signal indicating the amplitude level of said sounds; and
said method further includes the step of dynamically adjusting said gain in response to said highest mean level determined by said determining step (a).

8. A method as in claim 5 further including the steps of:
(a1) calculating the mean value of all of said sound amplitude levels stored by said storing step (5);
(a2) calculating the mean value of all of said stored amplitude levels stored by said storing step (5) which are less than the mean value calculated by said calculating step (a1); and
(a3) setting said predetermined threshold level to a value between said mean value calculated by said calculating step (a1) and the mean value calculated by said calculating step (a2).

9. A method as in claim 8 wherein said setting step (a3) comprises the step of setting said predetermined threshold level to be half of the sum of said mean value calculated by said calculating step (a1) and the mean value calculated by said calculating step (a2) to which the mean value calculated by said calculating step (a2) has been added.

10. A method as in claim 5 wherein:
said determining step (b) also determines whether at least one stored sound amplitude level measured immediately before said sound amplitude level measured latest in time before said time of the center of maximum Korotkoff sound activity which is less than said predetermined threshold level is also less than said threshold level; and
said determining step (d) also determines whether at least one stored sound amplitude level measured immediately after said stored sound amplitude level measured earliest in time after said time of the center of maximum Korotkoff sound activity which is less than said predetermined threshold level is also less than said threshold level.

11. A method as in claim 10 further including the steps of verifying that the cuff pressures associated with the respective stored sound amplitude levels determined in determining steps (b) and (d) are substantially at expected pressure values derived from said controlled rate of cuff deflation.

12. A method of automatically measuring the systolic and diastolic blood pressures of a subject, comprising the steps of:
(1) disposing an occluding cuff, a sound transducer and ECG electrodes on a subject;
(2) inflating the cuff to a pressure greater than the systolic blood pressure of said subject;
(3) linearly deflating said cuff at a controlled rate until the pressure within said cuff falls to less than the diastolic blood pressure of said subject;
(4) during said deflating step (3), continuously producing a first signal indicating the amplitude of sound detected by said sound transducer;
(5) during said deflating step (3), continuously producing a second signal indicating the pressure within said cuff;
(6) detecting the onset of each cardiac cycle of said subject in response to signals generated by said ECG electrodes;
(7) for each cardiac cycle detected by said detecting step (6) during deflation of said cuff, detecting the peak level PKS of said first signal;

(8) for each cardiac cycle detected by said detecting step (6) during deflation of said cuff, detecting the level PRE of said second signal at the time said peak level PKS is detected by said detecting step (7);

(9) for each cardiac cycle detected by said detecting step (6) during deflation of said cuff, storing said peak level PKS detected by said detecting step (7) and said level PRE detected by said detecting step (8);

(10) determining, in response to said stored peak levels PKS, a predetermined number of consecutive cardiac cycles generating the highest average peak level of said first signal;

(11) calculating the mean value AKSN of all of said peak levels PKS stored by said storing step (9);

(12) calculating the mean value ANOISE of all of said peak levels PKS stored by said storing step (9) which are less than said mean value AKSN calculated by said calculating step (11);

(13) calculating a threshold level $$K\text{-THRESHOLD} = \frac{AKSN - ANOISE}{2} + ANOISE;$$

(14) determining the stored peak level PKS measured for last cardiac cycle occurring before the center one of said predetermined number of consecutive cardiac cycles determined by said determining step (10) which is less than K-THRESHOLD;

(15) selecting said level PRE stored by said storing step (9) for said last cardiac cycle determined by said determining step (14) as the systolic blood pressure of said subject;

(16) determining the stored peak level PKS measured for the first cardiac cycle occurring after the center one of said predetermined number of consecutive cardiac cycles determined by said determining step (10) which is less than K-THRESHOLD; and

(17) selecting said level PRE stored by said storing step (9) for said first cardiac cycle determined by said determining step (16) as the diastolic blood pressure of said subject.

13. A system for automatically measuring at least one cardiovascular parameter of a subject comprising:
    means for producing a random value and for converting said random value to a time duration;
    means for timing said at least one time duration;
    means for measuring at least one cardiovascular parameter of a subject hen said duration timed by said timing means has elapsed;
    means for storing said parameter measured by said measuring means; and
    automatic sequencing means operatively connected to said random value producing and converting means, timing means, measuring means and storing means, for repeatedly causing, in sequence, (1) said random value producing and converting means to produce a random value and convert said random value to a time duration, (2) said timing means to time said time duration, (3) said measuring means to measure said cardiovascular at least one parameter after said time duration timed by said timing means has elapsed, and (4) said storing means to store said parameter produced by said producing means, to obtain a series of measurements of said at least one parameter.

14. A system as in claim 13 wherein:
    said sequencing means also determines whether random values produced by said random value producing and converting means fall within a predetermined range, and controls said random value producing and converting means to produce an additional random value when a produced random value is not within said predetermined range.

15. A system as in claim 14 further including means for programming said predetermined range.

16. A system as in claim 13 wherein:
    said measuring means includes:
        an occluding cuff disposed on said subject,
        means for selectively inflating said occluding cuff to a pressure in excess of the systolic blood pressure of said subject,
        means for continuously sensing the pressure of said cuff;
        means for controllably deflating said cuff; and
        means for sensing Korotkoff sounds produced by said subject; and
    said system further includes:
        serial storing means for storing analog indicia of said sensed sounds and pressure,
        means for producing digital signals representing the cardiovascular at least one parameter of said subject in response to the cuff pressure sensed by said pressure means and the Korotkoff sounds sensed by said sound sensing means, and
        solid state memory means for storing said digital signals representing said cardiovascular at least one parameter.

17. A system for automatically measuring the blood pressure of a subject comprising:
    means for inflating an occluding cuff disposed on said subject to a first predetermined pressure;
    means for deflating said cuff at a controlled rate until the pressure within said cuff falls to a second predetermined pressure less than said first pressure;
    means for sensing the pressure within said cuff;
    means for sensing the amplitude level of sounds generated by said subject as a result of said cuff deflation;
    means for periodically storing levels representing pressures sensed by said pressure sensing means and sound amplitude levels sensed by said sound amplitude level sensing means during deflation of said cuff; and
    means for selecting, in response to said sensed sound amplitude levels stored in said storing means, the stored pressure levels indicating the systolic and diastolic blood pressures of said subject, said selecting means comprising a digital signal processing means for:
        (a) determining the time of occurrence of a predetermined number of stored sound amplitude levels measured consecutively in time which have the highest mean level, said time of occurrence being the time of the center of maximum Korotkoff sound activity;
        (b) determining the stored sound amplitude level measured latest in time before said determined time of the center of maximum Korotkoff sound activity which is less than a predetermined threshold level;
        (c) selecting as the systolic blood pressure of said subjecting the stored pressure level measured simultaneously with said determined sound amplitude level measured latest in time;

(d) determining the stored sound amplitude level measured earliest in time after said determined time of the center of maximum Korotkoff sound activity which is less than said predetermined threshold level; and (e) selecting as the diastolic blood pressure of the subject the stored pressure level measured simultaneously with said determined earliest in time sound amplitude level.

18. A system as in claim 17 wherein:
said system further includes:
   means for sensing R-waves produced by the brain of said subject, and
   means for determining the peak sound amplitude level sensed by said sound amplitude level sensing means occurring between each pair of adjacent R-waves sensed by said R-wave sensing means; and
said storing means stores each of said sensed peak amplitude levels determined by said determining means together with the pressure sensed by said pressure sensing means occurring simultaneously with said each sensed peak amplitude levels.

19. A system as in claim 17 wherein:
said sound amplitude sensing means includes:
   means for detecting sound generated by said subject as a result of deflation of said cuff, and
   means for amplifying the sounds detected by said sound detecting means by a predetermined gain to produce a signal indicating the amplitude level of said sounds; and
said processing means also dynamically adjusts said gain in response to said determined highest mean level.

20. A system as in claim 17 wherein said processing means also:
   (a1) calculates the mean value of all of said sound amplitude levels stored by said storing means;
   (a2) calculates a further mean value of all of said stored amplitude levels stored by said storing means which are less than said calculated mean value of all of said stored sound amplitude levels; and
   (a3) sets said predetermined threshold level to a value between said mean value and said further mean value.

21. A system as in claim 20 wherein said processing means sets said predetermined threshold level to be half of the sum of said mean value and said further mean value to which the further mean value is added.

22. A system as in claim 17 wherein said processing means also:
   determines whether at least one stored sound amplitude level measured immediately before said sound, amplitude level measured latest in time before said determined time of the center of maximum Korotkoff sound activity which is less than said predetermined threshold level is also less than said threshold level; and
   determines whether at least one stored sound amplitude level measured immediately after said stored sound amplitude level measured earliest in time after said determined time of the center of maximum Korotkoff sound activity which is less than said predetermined threshold level is also less than said threshold level.

23. A system as in claim 17 further including means for verifying that the cuff pressures associated with the respective stored sound amplitude levels determined by said digital signal processing means are substantially at expected pressure values derived from said controlled rate of cuff deflation.

24. A system for automatically measuring the systolic and diastolic blood pressures of a subject, said system of the type including an occluding cuff, a Korotkoff sound transducer and ECG electrodes, said system comprising:
   means for inflating said cuff to a pressure greater than the systolic blood pressure of said subject;
   means for linearly deflating said cuff at a controlled rate until the pressure within said cuff falls to less than the diastolic blood pressure of said subject;
   means for continuously producing a first signal indicating the amplitude of sound detected by said Korotkoff sound transducer;
   means for continuously producing a second signal indicating the pressure within said cuff;
   means for detecting the onset of each cardiac cycle of said subject in response to signals generated by said ECG electrodes;
   storing means for storing digital signals; and
   digital signal processing means for:
   (a) determining the peak level PKS of said first signal for each cardiac cycle detected by said cardiac cycle detecting means,
   (b) determining the level PRE of said second signal at the time said peak level PKS is determined for each cardiac cycle detected by said cardiac cycle detecting means,
   (c) storing, in said storing means, said peak level PKS and said determined level PRE for each cardiac cycle detected by said cardiac cycle detecting means,
   (d) determining, in response to said peak levels PKS stored by said storing means, a predetermined number of consecutive cardiac cycles having the highest average peak level,
   (e) calculating the mean value AKSN of all of said peak levels PKS stored by said storing means,
   (f) calculating the mean value ANOISE of all of said peak levels PKS stored by said storing means which are less than said mean value AKSN,
   (g) calculating a threshold level $$K\text{-THRESHOLD} = \frac{AKSN - ANOISE}{2} + ANOISE;$$

(h) determining the stored peak level PKS measured for the last cardiac cycle occurring before the center cardiac cycle of said predetermined number of consecutive cardiac cycles determined to have the highest average peak level which is less than K-THRESHOLD,
   (i) selecting said level PRE stored by said storing means for said last cardiac cycle as the systolic blood pressure of said subject,
   (j) determining the stored peak level PKS measured for the first cardiac cycle occurring after the center cardiac cycle of said predetermined number of consecutive cardiac cycles determined to have the highest average peak level which is less than K-THRESHOLD, and
   (k) selecting said level PRE stored by said storing means for said first cardiac cycle as the diastolic blood pressure of said subject.

* * * * *